(12) United States Patent
Zhang et al.

(10) Patent No.: US 12,140,597 B2
(45) Date of Patent: **\*Nov. 12, 2024**

(54) THYROGLOBULIN QUANTITATION BY MASS SPECTROMETRY

(71) Applicant: Quest Diagnostics Investments Incorporated, Wilmington, DE (US)

(72) Inventors: Yanni Zhang, Mission Viejo, CA (US); Nigel J. Clarke, San Clemente, CA (US); Richard E Reitz, Las Vegas, NV (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,196

(22) Filed: Dec. 29, 2022

(65) Prior Publication Data
US 2023/0236200 A1 Jul. 27, 2023

Related U.S. Application Data

(63) Continuation of application No. 16/429,941, filed on Jun. 3, 2019, now Pat. No. 11,543,415, which is a
(Continued)

(51) Int. Cl.
G01N 33/68 (2006.01)
G01N 33/78 (2006.01)

(52) U.S. Cl.
CPC ......... G01N 33/6848 (2013.01); G01N 33/68 (2013.01); G01N 33/6893 (2013.01);
(Continued)

(58) Field of Classification Search
CPC ............... G01N 33/6848; G01N 33/68; G01N 33/6893; G01N 33/78; G01N 2800/52; G01N 2800/7028; Y10T 436/24
See application file for complete search history.

(56) References Cited

U.S. PATENT DOCUMENTS 6,107,623 A  8/2000 Bateman et al.
6,124,137 A  9/2000 Hutchens et al.
(Continued)

FOREIGN PATENT DOCUMENTS

WO  2004031730 A2  4/2004
WO  2008027861 A1  3/2008
(Continued)

OTHER PUBLICATIONS

Hoffman. Mass Spectrometry Principles and Applications. Third Edition (Year: 2007).*
(Continued)

*Primary Examiner* — Rebecca M Fritchman
(74) *Attorney, Agent, or Firm* — Foley & Lardner LLP

(57) ABSTRACT

Provided are methods for determining the amount of thyroglobulin in a sample using various purification steps followed by mass spectrometry. The methods generally involve purifying thyroglobulin in a test sample, digesting thyroglobulin to form peptide T129, purifying peptide T129, ionizing peptide T129, detecting the amount of peptide T129 ion generated, and relating the amount of peptide T129 ion to the amount of thyroglobulin originally present in the sample.

5 Claims, 15 Drawing Sheets

Specification includes a Sequence Listing.

Related U.S. Application Data continuation of application No. 14/726,957, filed on Jun. 1, 2015, now Pat. No. 10,309,971, which is a continuation of application No. 14/053,423, filed on Oct. 14, 2013, now Pat. No. 9,046,531, which is a continuation of application No. 13/859,551, filed on Apr. 9, 2013, now Pat. No. 8,574,915, which is a continuation of application No. 13/198,620, filed on Aug. 4, 2011, now Pat. No. 8,455,259, which is a continuation of application No. 12/001,076, filed on Dec. 6, 2007, now Pat. No. 8,030,084.

(52) U.S. Cl.
CPC ......... *G01N 33/78* (2013.01); *G01N 2800/52* (2013.01); *G01N 2800/7028* (2013.01); *Y10T 436/24* (2015.01)

(56) References Cited

U.S. PATENT DOCUMENTS

| | | |
|---|---|---|
| 6,204,500 B1 | 3/2001 | Whitehouse et al. |
| 6,268,144 B1 | 7/2001 | Koester |
| 7,632,686 B2 | 12/2009 | Anderson |
| 8,030,084 B2 | 10/2011 | Zhang et al. |
| 8,455,259 B2 | 6/2013 | Zhang et al. |
| 8,574,915 B2 | 11/2013 | Zhang et al. |
| 9,012,394 B2 | 4/2015 | Zhang et al. |
| 9,046,531 B2 | 6/2015 | Zhang et al. |
| 9,140,695 B2 | 9/2015 | Kushnir et al. |
| 9,274,124 B2 | 3/2016 | Anderson |
| 9,580,740 B2 | 2/2017 | Zhang et al. |
| 9,915,663 B2 | 3/2018 | Zhang et al. |
| 9,970,943 B2 | 5/2018 | Anderson |
| 10,191,064 B2 | 1/2019 | Zhang et al. |
| 2002/0042112 A1 | 4/2002 | Koster et al. |
| 2004/0072251 A1* | 4/2004 | Anderson ........ G01N 33/54306 435/7.1 |
| 2005/0064422 A1 | 3/2005 | Barnidge et al. |
| 2006/0223188 A1 | 10/2006 | Soldin |
| 2007/0105179 A1 | 5/2007 | Madson |
| 2007/0224628 A1 | 9/2007 | Gordon et al. |
| 2009/0042213 A1 | 2/2009 | Hoofnagle et al. |

FOREIGN PATENT DOCUMENTS

| | | |
|---|---|---|
| WO | 2011116028 A1 | 9/2011 |
| WO | 2012111249 A1 | 8/2012 |

OTHER PUBLICATIONS

Konerman. Unfolding of Proteins Monitored by Electrospray Ionization Mass Spectrometry: A Comparison of Positive and Negative Ion Modes. (Year: 1998).*

Persoon A.C., et al., "Clinical Utility of an Automated Immunochemiluminometric Thyroglobulin Assay in Differentiated Thyroid Carcinoma," Clinical Chemistry, 2006, vol. 52 (4), pp. 686-691.

Persoon A.C., et al., "Thyroblobulin (Tg) Recovery Testing with Quantitative Tg Antibody Measurement for Determining Interference in Serum Tg Assays in Differentiated Thyroid Carcinoma," Clinical Chemistry, 2006, vol. 52 (6), pp. 1196-1199.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Salek, "Analysis of Thyroblobulin Iodination by Tandem Mass Spectrometry Using Immonium Ions of Monoiodo- And Diiodo-Tyrosine," Proteomics, 2005, vol. 5 (2), pp. 351-353.

Salm P., et al., "The Quantification of Sirolimus by High-Performance Liquid Chromatography-Tandem Mass Spectrometry and Microparticle Enzyme Immunoassay in Renal Transplant Recipients," Clinical Therapeutics, 2000, vol. 22 Suppl B, pp. B71-B85.

Spencer C.A., et al., "Detection of Residual and Recurrent Differentiated Thyroid Carcinoma by Serum Thyroglobulin Measurement," Thyroid, 1999, vol. 9 (5), pp. 435-441.

Spencer C.A., et al., "Thyroglobulin Measurement Techniques, Clinical Benefits, and Pitfalls," Endocrinology Metabolism Clinics of North America , 1995, vol. 24 (4), pp. 841-863.

Steen H., et al., "The ABC's (and XYZ's) of Peptide Sequencing," Nature Reviews Molecular Cell Biology, 2004, vol. 5 (9), pp. 699-711.

Supplementary European Search Report for Application No. EP08860014, mailed on Jan. 28, 2011, 5 pages.

Tang X.J., et al., "An Investigation of Fragmentation Mechanisms of Doubly Protonated Tryptic Peptides," Rapid Communications in Mass Spectrometry, 1992, vol. 6 (11), pp. 651-677.

Taylor P.J., et al., "Simultaneous Quantification of Tacrolimus and Sirolimus in Human Blood, by High-Performance Liquid Chromatography—Tandem Mass Spectrometry," Therapeutic Drug Monitoring, 2000, vol. 22 (5), pp. 608-612.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US08/85435, mailed on Apr. 22, 2009, 5 Pages.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Biemann K., "Mass Spectrometry of Peptides and Proteins," Annual Review of Biochemistry, 1992, vol. 61, pp. 977-1010.

Bourrel F., et al., "Immunoradiometric Assay of Thyroglobulin in Patients with Differentiated Thyroid Carcinomas: Need for Thyroglobulin Recovery Tests," Clinical Chemistry and Laboratory Medicine, 1998, vol. 36 (8), pp. 725-730.

Di Jeso B., et al., "Mixed-Disulfide Folding Intermediates between Thyroglobulin and Endoplasmic Reticulum Resident Oxidoreductases ERp57 and protein Disulfide Isomerase," Molecular and Cellular Biology, 2005, vol. 25 (22), pp. 9793-9805.

Dunn A.D., et al., "Tyrosine 130 is an Important Outer Ring Donor for Thyroxine Formation in Thyroglobulin," The Journal of Biological Chemistry, 1998, vol. 273 (39), pp. 25223-25229.

Dunn J.T., et al., "The Sites of Thyroid Hormone Formation in Rabbit Thyroglobulin," The Journal of Biological Chemistry, 1987, vol. 262 (35), pp. 16948-16952.

European Search Report for Application No. EP13185360, mailed on Jan. 22, 2014, 7 pages.

Extended European Search Report for Application No. 13839646.0, mailed on Mar. 21, 2016, 11 pages.

Extended European Search Report for Application No. EP17200516.7, mailed on Jan. 30, 2018, 8 pages.

Extended European Search Report for Application No. EP18175367, mailed on Jul. 16, 2018, 10 pages.

Final Office Action mailed Apr. 1, 2022 for U.S. Appl. No. 16/429,941, filed Jun. 3, 2019.

Final Office Action mailed Aug. 1, 2016 for U.S. Appl. No. 14/726,957, filed Jun. 1, 2015.

Final Office Action mailed Sep. 6, 2012 for U.S. Appl. No. 13/198,620, filed Aug. 4, 2011.

Final Office Action mailed Jan. 25, 2011 for U.S. Appl. No. 12/001,076, filed Dec. 6, 2007.

Final Office Action mailed Sep. 25, 2017 for U.S. Appl. No. 14/726,957, filed Jun. 1, 2015.

Final Office Action mailed Jan. 26, 2021 for U.S. Appl. No. 16/429,941, filed Jun. 3, 2019.

Final Office Action mailed Aug. 27, 2014 for U.S. Appl. No. 14/053,423, filed Oct. 14, 2013.

Final Office Action mailed Oct. 27, 2010 for U.S. Appl. No. 12/001,076, filed Dec. 6, 2007.

(56) References Cited

OTHER PUBLICATIONS

Gentile F., et al., "Identification of Hormonogenic Tyrosines in Fragment 1218-1591 of Bovine Thyroglobulin By Mass Spectrometry. Hormonogenic Acceptor Tyr-1291 and Donor Tyr-1375," The Journal of Biological Chemistry, 1997, vol. 272 (1), pp. 639-646.
Guo-Zhong Ji, et al., "Clinical Test Diagnosis and Resolution" Jan. 2011, pp. 335-336.
Hoffman E. D., et al., "Mass Spectrometry: Principles and Applications," Third Edition, 2007, pp. 1-489.
Hoofnagle A.N., et al., "Quantification of Thyroglobulin, a Low-Abundance Serum Protein, by Immunoaffinity Peptide Enrichment and Tandem Mass Spectrometry," Clinical Chemistry, 2008, vol. 54 (11), pp. 1796-1804.
International Preliminary Report on Patentability for Application No. PCT/US2008/085435, mailed on Jun. 8, 2010.
International Search Report and Written Opinion for Application No. PCT/US2013/60659, mailed on Dec. 23, 2013, 10 pages.
International Search Report for Application No. PCT/US08/85435, mailed on Apr. 22, 2009, 2 Pages.
Kim P.S., et al., "Folding and Assembly of Newly Synthesized Thyroblobulin Occurs in a Pre-Golgi Compartment," The Journal of Biological Chemistry, 1991, vol. 266 (19), pp. 12412-12418.
Kushnir M.M., et al., "High Sensitivity Measurement of Thyroglobulin in Serum in Presence of Anti-Thyroglobulin Autoantibodies," May 15, 2012. Retrieved from the Internet: URL:https://www.aruplab.com/Research&Development/resources/Posters/2012/Kushnir_ASMS_0512.pdf.
Kushnir M.M., et al., "Mass Spectrometry Based Method for Accurate Measurement of Thyroglobulinin the Presence of Anti-Thyroglobulin Autoantibodies," May 15, 2012. Retrievedfrom the Internet: URL:https://www.aruplab.com/Research&Development/resources/Posters/2013/Kushnir_ENDO_0613.pdf.
Kushnir M.M., et al., "Measurement of Thyroglobulin by Liquid Chromatography—Tandem MassSpectrometry in Serum and Plasma in the Presence of Anti-thyroglobulin Autoantibodies," ClinicalChemistry, 2013, vol. 59(6), pp. 982-990.
"Screenshot of Google page", Mar. 10, 2016, XP055257300, Retrieved from the Internet: URL: www.google.com.
Learmonth M., et al., "Protein Identification by In-Gel Digestion and Mass Spectrometric Analysis," in: The Proteomics Protocols Handbook, 2005, Chapter 30, Walker J.M., ed., Humana Press, pp. 311-314.
Luo J.L., et al., "Diagnostic Value of Combing TG, TGAb and Cervical Ultrasonic Examination in the Recurrence or Metastasis Lesion of Differentiated Thyroid Carcinoma after Treatment," Chinese Journal of Clinicians (Electronic Edition), 2012, vol. 6 (3), pp. 580-583.
Mann M., et al., "Analysis of Proteins and Proteomes by Mass Spectrometry," Annual Review of Biochemistry, 2001, vol. 70, pp. 437-473.
Mann M., "Functional and Quantitative Proteomics Using SILAC," Nature Reviews Molecular Cell Biology, 2006, vol. 7 (12), pp. 952-958.
MEIKLA.W., et al., "Diagnosis and Management of Thyroid Nodules and Cancer Focus onThyroglobulin; Thyroglobulin and Thyroid Cancer: Part 2 of Presentation: Analytical Method and Performance", Nov. 16, 2012. Retrieved from theInternet: URL: http://arup.utah.edu/media/thyroidglobulin/thyroid.cancer.pgr.final.pdf.
Merchant M., et al., "Recent Advancements in Surface-Enhanced Laser Desorption/Ionization-Time of Flight-Mass Spectrometry," Electrophoresis, 2000, vol. 21 (6), pp. 1164-1167.
Non-Final Office Action mailed Jul. 8, 2020 for U.S. Appl. No. 16/429,941, filed Jun. 3, 2019.
Non-Final Office Action mailed Aug. 12, 2021 for U.S. Appl. No. 16/429,941, filed Jun. 3, 2019.
Non-Final Office Action mailed Jan. 12, 2016 for U.S. Appl. No. 14/726,957, filed Jun. 1, 2015.
Non-Final Office Action mailed Mar. 13, 2017 for U.S. Appl. No. 14/726,957, filed Jun. 1, 2015.
Non-Final Office Action mailed Jun. 16, 2017 for U.S. Appl. No. 15/443,805, filed Feb. 27, 2017.
Non-Final Office Action mailed Jun. 19, 2014 for U.S. Appl. No. 14/031,678, filed Sep. 19, 2013.
Non-Final Office Action mailed Oct. 21, 2019 for U.S. Appl. No. 16/259,696, filed Jan. 28, 2019.
Non-Final Office Action mailed Jan. 22, 2016 for U.S. Appl. No. 14/063,956, filed Oct. 25, 2013.
Non-Final Office Action mailed Dec. 23, 2013 for U.S. Appl. No. 14/053,423, filed Oct. 14, 2013.
Non-Final Office Action mailed Apr. 27, 2016 for U.S. Appl. No. 14/689,542, filed Apr. 14, 2015.
Non-Final Office Action mailed Apr. 28, 2010 for U.S. Appl. No. 12/001,076, filed Dec. 6, 2007.
Non-Final Office Action mailed May 29, 2018 for U.S. Appl. No. 15/906,078, filed Feb. 27, 2018.
Non-Final Office Action mailed Nov. 30, 2011 for U.S. Appl. No. 13/198,620, filed Aug. 4, 2011.
Olsen J.V., et al., "Trypsin Cleaves Exclusively C-Terminal to Arginine and Lysine Residues," Molecular Cellular Proteomics, 2004, vol. 3 (6), pp. 608-614.

* cited by examiner

Figure 1

P01266 Sequence

```
MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCVGFYQEQAGSLACVPCPVGRTTI
SAGAFSQTHCVTDCQRNEAGLQCDQNGQYRASQKDRGSGKAFCVDGEGRRLPWWETEAPL
EDSQCLMMQKFEKVPESKVIFDANAPVAVRSKVPDSEFPVMQCLTDCTEDEACSFFTVST
TEPEISCDFYAWTSDNVACMTSDQKRDALGNSKATSFGSLRCQVKVRSHGQDSPAVYLKK
GQGSTTTLQKRFEPTGFQNMLSGLYNPIVFSASGANLTDAHLFCLLACDRDLCCDGFVLT
QVQGGAIICGLLSSPSVLLCNVKDWMDPSEAWANATCPGVTYDQESHQVILRLGDQEFIK
SLTPLEGTQDTFTNFQQVYLWKDSDMGSRPESMGCRKDTVPRPASPTEAGLTTELFSPVD
LNQVIVNGNQSLSSQKHWLFKHLFSAQQANLWCLSRCVQEHSFCQLAEITESASLYFTCT
LYPEAQVCDDIMESNAQGCRLILPQMPKALFRKKVILEDKVKNFYTRLPFQKLMGISIRN
KVPMSEKSISNGFFECERRCDADPCCTGFGFLNVSQLKGGEVTCLTLNSLGIQMCSEENG
GAWRILDCGSPDIEVHTYPFGWYQKPIAQNNAPSFCPLVVLPSLTEKVSLDSWQSLALSS
VVVDPSIRHFDVAHVSTAATSNFSAVRDLCLSECSQHEACLITTLQTQPGAVRCMFYADT
QSCTHSLQGQNCRLLLREEATHIYRKPGISLLSYEASVPSVPISTHGRLLGRSQAIQVGT
SWKQVDQFLGVPYAAPPLAERRFQAPEPLNWTGSWDASKPRASCWQPGTRTSTSPGVSED
CLYLNVFIPQNVAPNASVLVFFHNTMDREESEGWPAIDGSFLAAVGNLIVVTASYRVGVF
GFLSSGSGEVSGNWGLLDQVAALTWVQTHIRGFGGDPRRVSLAADRGGADVASIHLLTAR
ATNSQLFRRAVLMGGSALSPAAVISHERAQQQAIALAKEVSCPMSSSQEVVSCLRQKPAN
VLNDAQTKLLAVSGPFHYWGPVIDGHFLREPPARALKRSLWVEVDLLIGSSQDDGLINRA
KAVKQFEESRGRTSSKTAFYQALQNSLGGEDSDARVEAAATWYYSLEHSTDDYASFSRAL
ENATRDYFIICPIIDMASAWAKRARGNVFMYHAPENYGHGSLELLADVQFALGLPFYPAY
EGQFSLEEKSLSLKIMQYFSHFIRSGNPNYPYEFSRKVPTFATPWPDFVPRAGGENYKEF
SELLPNRQGLKKADCSFWSKYISSLKTSADGAKGGQSAESEEEELTAGSGLREDLLSLQE
PGSKTYSK
```

Figure 2

P01266-2 Isoform 2 Sequence

```
>sp_vs|P01266-2|THYG_HUMAN Isoform 2 of P01266 - Homo sapiens (Human)
MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHLMQKFEKVPESKVIFDANAPVAVRSKVPDSEFPVMQCLTDCTEDEACSFFT
VSTTEPEISCDFYAWTSDNVACMTSDQKRDALGNSKATSFGSLRCQVKVRSHGQDSPAVY
LKKGQGSTTTLQKRFEPTGFQNMLSGLYNPIVFSASGANLTDAHLFCLLACDRDLCCDGF
VLTQVQGGAIICGLLSSPSVLLCNVKDWMDPSEAWANATCPGVTYDQESHQVILRLGDQE
FIKSLTPLEGTQDTFTNFQQVYLWKDSDMGSRPESMGCRKDTVPRPASPTEAGLTTELFS
PVDLNQVIVNGNQSLSSQKHWLFKHLFSAQQANLWCLSRCVQEHSFCQLAEITESASLYF
TCTLYPEAQVCDDIMESNAQGCRLILPQMPKALFRKKVILEDKVKNFYTRLPFQKLMGIS
IRNKVPMSEKSISNGFFECERRCDADPCCTGFGFLNVSQLKGGEVTCLTLNSLGIQMCSE
ENGGAWRILDCGSPDIEVHTYPFGWYQKPIAQNNAPSFCPLVVLPSLTEKVSLDSWQSLA
LSSVVVDPSIRHFDVAHVSTAATSNFSAVRDLCLSECSQHEACLITTLQTQPGAVRCMFY
ADTQSCTHSLQGQNCRLLLREEATHIYRKPGISLLSYEASVPSVPISTHGRLLGRSQAIQ
VGTSWKQVDQFLGVPYAAPPLAERRFQAPEPLNWTGSWDASKPRASCWQPGTRTSTSPGV
SEDCLYLNVFIPQNVAPNASVLVFFHNTMDREESEGWPAIDGSFLAAVGNLIVVTASYRV
GVFGFLSSGSGEVSGNWGLLDQVAALTWVQTHIRGFGGDPRRVSLAADRGGADVASIHLL
TARATNSQLFRRAVLMGGSALSPAAVISHERAQQQAIALAKEVSCPMSSSQEVVSCLRQK
PANVLNDAQTKLLAVSGPFHYWGPVIDGHFLREPPARALKRSLWVEVDLLIGSSQDDGLI
NRAKAVKQFEESRGRTSSKTAFYQALQNSLGGEDSDARVEAAATWYYSLEHSTDDYASFS
RALENATRDYFIICPIIDMASAWAKRARGNVFMYHAPENYGHGSLELLADVQFALGLPFY
PAYEGQFSLEEKSLSLKIMQYFSHFIRSGNPNYPYEFSRKVPTFATPWPDFVPRAGGENY
KEFSELLPNRQGLKKADCSFWSKYISSLKTSADGAKGGQSAESEEEELTAGSGLREDLLS
LQEPGSKTYSK
```

Figure 3

Q59GF0 (Tg variant-Fragment) Sequence
>Q59GF0|Q59GF0_HUMAN Thyroglobulin variant (Fragment) - Homo sapiens (Human).
IPRKPISKRPVRPSLPRSPRCPLPFNASEVVGGTILCETISGPTGSAMQQCQLLCRQGSW
SVFPPGPLICSLESGRWESQLPQPRACQRPQLWQTIQTQGHFQLQLPPGKMCSADYAGLL
QTFQVFILDELTARGFCQIQVKTFGTLVSIPVCNNSSVQVGCLTRERLGVNVTWKSRLED
IPVASLPDLHDIERALVGKDLLGRFTDLIQSGSFQLHLDSKTFPAETIRFLQGDHFGTSP
RTWFGCSEGFYQVLTSEASQDGLGCVKCPEGSYSQDEECIPCPVGFYQEQAGSLACVPCP
VGRTTISAGAFSQTHCVTDCQRNEAGLQCDQNGQYRASQKDRGSGKAFCVDGEGRRLPWW
ETEAPLEDSQCLMMQKFEKVPESKVIFDANAPVAVRSKVPDSEFPVMQCLTDCTEDEACS
FFTVSTTEPEISCDFYAWTSDNVACMTSDQKRDALGNSKATSFGSLRCQVKVRSHGQDSP
AVYLKKGQGSTTTLQKRFEPTGFQNMLSGLYNPIVFSASGANLTDAHLFCLLACDRDLCC
DGFVLTQVQGGAIICGLLSSPSVLLCNVKDWMDPSEAWANATCPGVTYDQESHQVILRLG
DQEFIKSLTPLEGTQDTFTNFQQVYLWKDSDMGSRPESMGCRKNTVPRPASPTEAGLTTE
LFSPVDLNQVIVNGNQSLSSQKHWLFKHLFSAQQANLWCLSRCVQEHSFCQLAEITESAS
LYFTCTLYPEAQVCDDIMESNAQGCRLILPQMPKALFRKKVILEDKVKNFYTRLPFQKLT
GISIRNKVPMSEKSISNGFFECERRCDADPCCTGFGFLNVSQLKGGEVTCLTLNSLGIQM
CSEENGGAWRILDCGSPDIEVHTYPFGWYQKPIAQNNAPSFCPLVVLPSLTEKVSLDSWQ
SLALSSVVVDPSIRHFDVAHVSTAATSNFSAVRDLCLSECSQHEACLITTLQTQPGAVRC
MFYADTQSCTHSLQGQNCRLLLREEATHIYRKPGISLLSYEASVPSVPISTHGRLLGRSQ
AIQVGTSWKQVDQFLGVPYAAPPLAERRFQAPEPLNWTGSWDASKPRASCWQPGTRTSTS
PGVSEDCLYLNVFIPQNVAPNASVLVFFHNTMDREESEGWPAIDGSFLAAVGNLIVVTAS
YRVGVFGFLSSGSGEVSGNWGLLDQVAALTWVQTHIRGFGGDPRRVSLAADRGGADVASI
HLLTARATNSQLFRRAVLMGGSALSPAAVISHERAQQQAIALAKEVSCPMSSSQEVVSCL
RQKPANVLNDAQTKLLAVSGPFHYWGPVIDGHFLREPPARALKRSLWVEVDLLIGSSQDD
GLINRAKAVKQFEESQGRTSSKTAFYQALQNSLGGEDSDARVEAAATWYYSLEHSTDDYA
SFSRALENATRDYFIICPIIDMASAWAKRARGNVFMYHAPENYGHGSLELLADVQFALGL
PFYPAYEGQFSLEEKSLSLKIMQYFSHFIRSGNPNYPYEFSRKVPTFATPWPDFVPRAGG
ENYKEFSELLPNRQGLKKADCSFWSKYISSLKTSADGAKGGQSAESEEEELTAGSGLRED
LLSLQEPGSKTYSK

Figure 4A (1 of 7)

```
          10         20         30         40         50         60
   MALVLEIFTL LASICWVSAN IFEYQVDAQP LRPCELQRET AFLKQADYVP QCAEDGSFQT
   MALVLEIFTL LASICWVSAN IFEYQVDAQP LRPCELQRET AFLKQADYVP QCAEDGSFQT 70         80         90        100        110        120
   VQCQNDGRSC WCVGANGSEV LGSRQPGRPV ACLSFCQLQK QQILLSGYIN STDTSYLPQC
   VQCQNDGRSC WCVGANGSEV LGSRQPGRPV ACLSFCQLQK QQILLSGYIN STDTSYLPQC 130        140        150        160        170        180
   QDSGDYAPVQ CDVQQVQCWC VDAEGMEVYG TRQLGRPKRC PRSCEIRNRR LLHGVGDKSP
   QDSGDYAPVQ CDVQQVQCWC VDAEGMEVYG TRQLGRPKRC PRSCEIRNRR LLHGVGDKSP 190        200        210        220        230        240
   PQCSAEGEFM PVQCKFVNTT DMMIFDLVHS YNRFPDAFVT FSSFQRRFPE VSGYCHCADS
   PQCSAEGEFM PVQCKFVNTT DMMIFDLVHS YNRFPDAFVT FSSFQRRFPE VSGYCHCADS 250        260        270        280        290        300
   QGRELAETGL ELLLDEIYDT IFAGLDLPST FTETTLYRIL QRRFLAVQSV ISGRFRCPTK
   QGRELAETGL ELLLDEIYDT IFAGLDLPST FTETTLYRIL QRRFLAVQSV ISGRFRCPTK 310        320        330        340        350        360
   CEVERFTATS FGHPYVPSCR RNGDYQAVQC QTEGPCWCVD AQGKEMHGTR QQGEPPSCAE
   CEVERFTATS FGHPYVPSCR RNGDYQAVQC QTEGPCWCVD AQGKEMHGTR QQGEPPSCAE 370        380        390        400        410        420
   GQSCASERQQ ALSRLYFGTS GYFSQHDLFS SPEKRWASPR VARFATSCPP TIKELFVDSG
   GQSCASERQQ ALSRLYFGTS GYFSQHDLFS SPEKRWASPR VARFATSCPP TIKELFVDSG 430        440        450        460        470        480
   LLRPMVEGQS QQFSVSENLL KEAIRAIFPS RGLARLALQF TTNPKRLQQN LFGGKFLVNV
   LLRPMVEGQS QQFSVSENLL KEAIRAIFPS RGLARLALQF TTNPKRLQQN LFGGKFLVNV
```

Figure 4B (2 of 7)

```
              490        500        510        520        530        540
         GQFNLSGALG TRGTFNFSQF FQQLGLASFL NGGRQEDLAK PLSVGLDSNS STGTPEAAKK
         GQFNLSGALG TRGTFNFSQF FQQLGLASFL NGGRQEDLAK PLSVGLDSNS STGTPEAAKK 550        560        570        580        590        600
         DGTMNKPTVG SFGFEINLQE NQNALKFLAS LLELPEFLLF LQHAISVPED VARDLGDVME
         DGTMNKPTVG SFGFEINLQE NQNALKFLAS LLELPEFLLF LQHAISVPED VARDLGDVME 610        620        630        640        650        660
         TVLSSQTCEQ TPERLFVPSC TTEGSYEDVQ CFSGECWCVN SWGKELPGSR VRGGQPRCPT
         TVLSSQTCEQ TPERLFVPSC TTEGSYEDVQ CFSGECWCVN SWGKELPGSR VRGGQPRCPT 670        680        690        700        710        720
         DCEKQRARMQ SLMGSQPAGS TLFVPACTSE GHFLPVQCFN SECYCVDAEG QAIPGTRSAI
         DCEKQRARMQ SLMGSQPAGS TLFVPACTSE GHFLPVQCFN SECYCVDAEG QAIPGTRSAI 730        740        750        760        770        780
         GKPKKCPTPC QLQSEQAFLR TVQALLSNSS MLPTLSDTYI PQCSTDGQWR QVQCNGPPEQ
         GKPKKCPTPC QLQSEQAFLR TVQALLSNSS MLPTLSDTYI PQCSTDGQWR QVQCNGPPEQ 790        800        810        820        830        840
         VFELYQRWEA QNKGQDLTPA KLLVKIMSYR EAASGNFSLF IQSLYEAGQQ DVFPVLSQYP
         VFELYQRWEA QNKGQDLTPA KLLVKIMSYR EAASGNFSLF IQSLYEAGQQ DVFPVLSQYP 850        860        870        880        890        900
         SLQDVPLAAL EGKRPQPREN ILLEPYLFWQ ILNGQLSQYP GSYSDFSTPL AHFDLRNCWC
         SLQDVPLAAL EGKRPQPREN ILLEPYLFWQ ILNGQLSQYP GSYSDFSTPL AHFDLRNCWC 910        920        930        940        950        960
         VDEAGQELEG MRSEPSKLPT CPGSCEEAKL RVLQFIRETE EIVSASNSSR FPLGESFLVA
         VDEAGQELEG MRSEPSKLPT CPGSCEEAKL RVLQFIRETE EIVSASNSSR FPLGESFLVA
```

Figure 4C (3 of 7)

```
           970        980        990       1000       1010       1020
      KGIRLRNEDL GLPPLFPPRE AFAEQFLRGS DYAIRLAAQS TLSFYQRRRF SPDDSAGASA
      KGIRLRNEDL GLPPLFPPRE AFAEQFLRGS DYAIRLAAQS TLSFYQRRRF SPDDSAGASA 1030       1040       1050       1060       1070       1080
      LLRSGPYMPQ CDAFGSWEPV QCHAGTGHCW CVDEKGGFIP GSLTARSLQI PQCPTTCEKS
      LLRSGPYMPQ CDAFGSWEPV QCHAGTGHCW CVDEKGGFIP GSLTARSLQI PQCPTTCEKS 1090       1100       1110       1120       1130       1140
      RTSGLLSSWK QARSQENPSP KDLFVPACLE TGEYARLQAS GAGTWCVDPA SGEELRPGSS
      RTSGLLSSWK QARSQENPSP KDLFVPACLE TGEYARLQAS GAGTWCVDPA SGEELRPGSS 1150       1160       1170       1180       1190       1200
      SSAQCPSLCN VLKSGVLSRR VSPGYVPACR AEDGGFSPVQ CDQAQGSCWC VMDSGEEVPG
      SSAQCPSLCN VLKSGVLSRR VSPGYVPACR AEDGGFSPVQ CDQAQGSCWC VMDSGEEVPG
                                                                 IPRKPI 1210       1220       1230       1240       1250       1260
      TRVTGGQPAC ESPRCPLPFN ASEVVGGTIL CETISGPTGS AMQQCQLLCR QGSWSVFPPG
      TRVTGGQPAC ESPRCPLPFN ASEVVGGTIL CETISGPTGS AMQQCQLLCR QGSWSVFPPG
      SKRPVRPSLP RSPRCPLPFN ASEVVGGTIL CETISGPTGS AMQQCQLLCR QGSWSVFPPG 1270       1280       1290       1300       1310       1320
      PLICSLESGR WESQLPQPRA CQRPQLWQTI QTQGHFQLQL PPGKMCSADY ADLLQTFQVF
      PLICSLESGR WESQLPQPRA CQRPQLWQTI QTQGHFQLQL PPGKMCSADY ADLLQTFQVF
      PLICSLESGR WESQLPQPRA CQRPQLWQTI QTQGHFQLQL PPGKMCSADY AGLLQTFQVF 1330       1340       1350       1360       1370       1380
      ILDELTARGF CQIQVKTFGT LVSIPVCNNS SVQVGCLTRE RLGVNVTWKS RLEDIPVASL
      ILDELTARGF CQIQVKTFGT LVSIPVCNNS SVQVGCLTRE RLGVNVTWKS RLEDIPVASL
      ILDELTARGF CQIQVKTFGT LVSIPVCNNS SVQVGCLTRE RLGVNVTWKS RLEDIPVASL
```

Figure 4D (4 of 7)

```
          1390       1400       1410       1420       1430       1440
    PDLHDIERAL VGKDLLGRFT DLIQSGSFQL HLDSKTFPAE TIRFLQGDHF GTSPRTWFGC
    PDLHDIERAL VGKDLLGRFT DLIQSGSFQL HLDSKTFPAE TIRFLQGDHF GTSPRTWFGC
    PDLHDIERAL VGKDLLGRFT DLIQSGSFQL HLDSKTFPAE TIRFLQGDHF GTSPRTWFGC 1450       1460       1470       1480       1490       1500
    SEGFYQVLTS EASQDGLGCV KCPEGSYSQD EECIPCPVGF YQEQAGSLAC VPCPVGRTTI
    SEGFYQVLTS EASQDGLGCV KCPEGSYSQD EECIPCPVGF YQEQAGSLAC VPCPVGRTTI
    SEGFYQVLTS EASQDGLGCV KCPEGSYSQD EECIPCPVGF YQEQAGSLAC VPCPVGRTTI 1510       1520       1530       1540       1550       1560
    SAGAFSQTHC VTDCQRNEAG LQCDQNGQYR ASQKDRGSGK AFCVDGEGRR LPWWETEAPL
    SAGAFSQTHL
    SAGAFSQTHC VTDCQRNEAG LQCDQNGQYR ASQKDRGSGK AFCVDGEGRR LPWWETEAPL 1570       1580       1590       1600       1610       1620
    EDSQCLMMQK FEKVPESKVI FDANAPVAVR SKVPDSEFPV MQCLTDCTED EACSFFTVST
           MQK FEKVPESKVI FDANAPVAVR SKVPDSEFPV MQCLTDCTED EACSFFTVST
    EDSQCLMMQK FEKVPESKVI FDANAPVAVR SKVPDSEFPV MQCLTDCTED EACSFFTVST 1630       1640       1650       1660       1670       1680
    TEPEISCDFY AWTSDNVACM TSDQKRDALG NSKATSFGSL RCQVKVRSHG QDSPAVYLKK
    TEPEISCDFY AWTSDNVACM TSDQKRDALG NSKATSFGSL RCQVKVRSHG QDSPAVYLKK
    TEPEISCDFY AWTSDNVACM TSDQKRDALG NSKATSFGSL RCQVKVRSHG QDSPAVYLKK 1690       1700       1710       1720       1730       1740
    GQGSTTTLQK RFEPTGFQNM LSGLYNPIVF SASGANLTDA HLFCLLACDR DLCCDGFVLT
    GQGSTTTLQK RFEPTGFQNM LSGLYNPIVF SASGANLTDA HLFCLLACDR DLCCDGFVLT
    GQGSTTTLQK RFEPTGFQNM LSGLYNPIVF SASGANLTDA HLFCLLACDR DLCCDGFVLT 1750       1760       1770       1780       1790       1800
    QVQGGAIICG LLSSPSVLLC NVKDWMDPSE AWANATCPGV TYDQESHQVI LRLGDQEFIK
    QVQGGAIICG LLSSPSVLLC NVKDWMDPSE AWANATCPGV TYDQESHQVI LRLGDQEFIK
    QVQGGAIICG LLSSPSVLLC NVKDWMDPSE AWANATCPGV TYDQESHQVI LRLGDQEFIK
```

Figure 4E (5 of 7)

```
           1810       1820       1830       1840       1850       1860
      SLTPLEGTQD TFTNFQQVYL WKDSDMGSRP ESMGCRKDTV PRPASPTEAG LTTELFSPVD
      SLTPLEGTQD TFTNFQQVYL WKDSDMGSRP ESMGCRKDTV PRPASPTEAG LTTELFSPVD
      SLTPLEGTQD TFTNFQQVYL WKDSDMGSRP ESMGCRKNTV PRPASPTEAG LTTELFSPVD 1870       1880       1890       1900       1910       1920
      LNQVIVNGNQ SLSSQKHWLF KHLFSAQQAN LWCLSRCVQE HSFCQLAEIT ESASLYFTCT
      LNQVIVNGNQ SLSSQKHWLF KHLFSAQQAN LWCLSRCVQE HSFCQLAEIT ESASLYFTCT
      LNQVIVNGNQ SLSSQKHWLF KHLFSAQQAN LWCLSRCVQE HSFCQLAEIT ESASLYFTCT 1930       1940       1950       1960       1970       1980
      LYPEAQVCDD IMESNAQGCR LILPQMPKAL FRKKVILEDK VKNFYTRLPF QKLMGISIRN
      LYPEAQVCDD IMESNAQGCR LILPQMPKAL FRKKVILEDK VKNFYTRLPF QKLMGISIRN
      LYPEAQVCDD IMESNAQGCR LILPQMPKAL FRKKVILEDK VKNFYTRLPF QKLTGISIRN 1990       2000       2010       2020       2030       2040
      KVPMSEKSIS NGFFECERRC DADPCCTGFG FLNVSQLKGG EVTCLTLNSL GIQMCSEENG
      KVPMSEKSIS NGFFECERRC DADPCCTGFG FLNVSQLKGG EVTCLTLNSL GIQMCSEENG
      KVPMSEKSIS NGFFECERRC DADPCCTGFG FLNVSQLKGG EVTCLTLNSL GIQMCSEENG 2050       2060       2070       2080       2090       2100
      GAWRILDCGS PDIEVHTYPF GWYQKPIAQN NAPSFCPLVV LPSLTEKVSL DSWQSLALSS
      GAWRILDCGS PDIEVHTYPF GWYQKPIAQN NAPSFCPLVV LPSLTEKVSL DSWQSLALSS
      GAWRILDCGS PDIEVHTYPF GWYQKPIAQN NAPSFCPLVV LPSLTEKVSL DSWQSLALSS 2110       2120       2130       2140       2150       2160
      VVVDPSIRHF DVAHVSTAAT SNFSAVRDLC LSECSQHEAC LITTLQTQPG AVRCMFYADT
      VVVDPSIRHF DVAHVSTAAT SNFSAVRDLC LSECSQHEAC LITTLQTQPG AVRCMFYADT
      VVVDPSIRHF DVAHVSTAAT SNFSAVRDLC LSECSQHEAC LITTLQTQPG AVRCMFYADT
```

Figure 4F (6 of 7)

```
          2170       2180       2190       2200       2210       2220
     QSCTHSLQGQ NCRLLLREEA THIYRKPGIS LLSYEASVPS VPISTHGRLL GRSQAIQVGT
     QSCTHSLQGQ NCRLLLREEA THIYRKPGIS LLSYEASVPS VPISTHGRLL GRSQAIQVGT
     QSCTHSLQGQ NCRLLLREEA THIYRKPGIS LLSYEASVPS VPISTHGRLL GRSQAIQVGT 2230       2240       2250       2260       2270       2280
     SWKQVDQFLG VPYAAPPLAE RRFQAPEPLN WTGSWDASKP RASCWQPGTR TSTSPGVSED
     SWKQVDQFLG VPYAAPPLAE RRFQAPEPLN WTGSWDASKP RASCWQPGTR TSTSPGVSED
     SWKQVDQFLG VPYAAPPLAE RRFQAPEPLN WTGSWDASKP RASCWQPGTR TSTSPGVSED 2290       2300       2310       2320       2330       2340
     CLYLNVFIPQ NVAPNASVLV FFHNTMDREE SEGWPAIDGS FLAAVGNLIV VTASYRVGVF
     CLYLNVFIPQ NVAPNASVLV FFHNTMDREE SEGWPAIDGS FLAAVGNLIV VTASYRVGVF
     CLYLNVFIPQ NVAPNASVLV FFHNTMDREE SEGWPAIDGS FLAAVGNLIV VTASYRVGVF 2350       2360       2370       2380       2390       2400
     GFLSSGSGEV SGNWGLLDQV AALTWVQTHI RGFGGDPRRV SLAADRGGAD VASIHLLTAR
     GFLSSGSGEV SGNWGLLDQV AALTWVQTHI RGFGGDPRRV SLAADRGGAD VASIHLLTAR
     GFLSSGSGEV SGNWGLLDQV AALTWVQTHI RGFGGDPRRV SLAADRGGAD VASIHLLTAR 2410       2420       2430       2440       2450       2460
     ATNSQLFRRA VLMGGSALSP AAVISHERAQ QQAIALAKEV SCPMSSSQEV VSCLRQKPAN
     ATNSQLFRRA VLMGGSALSP AAVISHERAQ QQAIALAKEV SCPMSSSQEV VSCLRQKPAN
     ATNSQLFRRA VLMGGSALSP AAVISHERAQ QQAIALAKEV SCPMSSSQEV VSCLRQKPAN 2470       2480       2490       2500       2510       2520
     VLNDAQTKLL AVSGPFHYWG PVIDGHFLRE PPARALKRSL WVEVDLLIGS SQDDGLINRA
     VLNDAQTKLL AVSGPFHYWG PVIDGHFLRE PPARALKRSL WVEVDLLIGS SQDDGLINRA
     VLNDAQTKLL AVSGPFHYWG PVIDGHFLRE PPARALKRSL WVEVDLLIGS SQDDGLINRA
```

Figure 4G (7 of 7)

```
       2530        2540        2550        2560        2570        2580
KAVKQFEESR  GRTSSKTAFY  QALQNSLGGE  DSDARVEAAA  TWYYSLEHST  DDYASFSRAL
KAVKQFEESR  GRTSSKTAFY  QALQNSLGGE  DSDARVEAAA  TWYYSLEHST  DDYASFSRAL
KAVKQFEESQ  GRTSSKTAFY  QALQNSLGGE  DSDARVEAAA  TWYYSLEHST  DDYASFSRAL 2590        2600        2610        2620        2630        2640
ENATRDYFII  CPIIDMASAW  AKRARGNVFM  YHAPENYGHG  SLELLADVQF  ALGLPFYPAY
ENATRDYFII  CPIIDMASAW  AKRARGNVFM  YHAPENYGHG  SLELLADVQF  ALGLPFYPAY
ENATRDYFII  CPIIDMASAW  AKRARGNVFM  YHAPENYGHG  SLELLADVQF  ALGLPFYPAY 2650        2660        2670        2680        2690        2700
EGQFSLEEKS  LSLKIMQYFS  HFIRSGNPNY  PYEFSRKVPT  FATPWPDFVP  RAGGENYKEF
EGQFSLEEKS  LSLKIMQYFS  HFIRSGNPNY  PYEFSRKVPT  FATPWPDFVP  RAGGENYKEF
EGQFSLEEKS  LSLKIMQYFS  HFIRSGNPNY  PYEFSRKVPT  FATPWPDFVP  RAGGENYKEF 2710        2720        2730        2740        2750        2760
SELLPNRQGL  KKADCSFWSK  YISSLKTSAD  GAKGGQSAES  EEEELTAGSG  LREDLLSLQE
SELLPNRQGL  KKADCSFWSK  YISSLKTSAD  GAKGGQSAES  EEEELTAGSG  LREDLLSLQE
SELLPNRQGL  KKADCSFWSK  YISSLKTSAD  GAKGGQSAES  EEEELTAGSG  LREDLLSLQE

PGSKTYSK
PGSKTYSK
PGSKTYSK
```

THYROGLOBULIN QUANTITATION BY MASS SPECTROMETRY

CROSS REFERENCE TO RELATED PATENT APPLICATIONS

This application is a Continuation of U.S. application Ser. No. 16/429,941, filed Jun. 3, 2019, now U.S. Pat. No. 11,543,415, which is a Continuation of U.S. application Ser. No. 14/726,957, filed Jun. 1, 2015, now U.S. Pat. No. 10,309,971, which is a Continuation of U.S. application Ser. No. 14/053,423, filed Oct. 14, 2103, now U.S. Pat. No. 9,046,531, which is a Continuation of U.S. application Ser. No. 13/859,551, filed Apr. 9, 2013, now U.S. Pat. No. 8,574,915, which is a Continuation of U.S. application Ser. No. 13/198,620, filed Aug. 4, 2011, now U.S. Pat. No. 8,455,259, which is a Continuation of U.S. application Ser. No. 12/001,076, filed Dec. 6, 2007, now U.S. Pat. No. 8,030,084, the entire contents of each of which are incorporated by reference herein.

SEQUENCE LISTING

The instant application contains a Sequence Listing which has been submitted in XML format via EFS-Web and is hereby incorporated by reference in its entirety. Said XML copy, created on Dec. 21, 2022, is named 054769-0504_SeqList.xml and is 12 KB bytes in size.

FIELD OF THE INVENTION

The invention relates to the quantitation of thyroglobulin. In a particular aspect, the invention relates to methods for quantitation of thyroglobulin by mass spectrometry.

BACKGROUND OF THE INVENTION

The following description of the background of the invention is provided simply as an aid in understanding the invention and is not admitted to describe or constitute prior art to the invention.

Thyroglobulin, or Tg, is a large dimeric secretary glycoprotein with a molecular weight of 660 kDa comprised of noncovalently bound homodimers.

Tg molecules exist in several forms. The three major Tg molecule sequences as found in the UniProt Knowledgebase (Swiss-Prot+TrEMBL) are P01266 (Human Thyroglobulin Precursor), P01266-2 (Isoform 2 of P01266), and Q59GF02 (Human Thyroglobulin Variant). (See FIGS. 1, 2, and 3, respectively.)

P01266 is the major variant of P01266 with a length of 2768 AA; P01266-2 is an isoform of P01266 with a length of 2711 AA. P01266-2 varies from P01266 at amino acid positions 1510 to 1567 of Tg; and Q59GF0 is a thyroglobulin fragment with a length of 1574 AA. Q59GF0 contains amino acids from positions 1212 to 2768 of Tg.

Tg can only be produced in the thyroid gland and may be produced by either normal well differentiated benign thyroid cells or thyroid cancer cells. It is the precursor protein for thyroid hormone syntheses and serves as the matrix for thyroid iodine storage. Tg is used by the thyroid gland to produce the thyroid hormones thyroxine (T4) and triiodothyronine (T3). Tg levels in the blood can be used as a tumor marker for differentiated thyroid carcinoma (DTC). A high level of Tg in the blood is not by itself an indicator of thyroid cancer, but persistence of Tg in the blood following surgical removal of the thyroid gland indicates persistence of thyroid tissue. A course of treatment following detection of Tg in the blood following surgical removal of the thyroid gland may include administration of radioiodine to ablate all remaining normal thyroid. Continued persistence of Tg in the blood following ablation of all normal thyroid could indicate that some amount of tumor is still present.

Several methods for quantitation of Tg have been developed. For example Spencer, et al., Thyroid, 1999, 9(5):435-41 and Persoon, et al., Clinical Chem 2006, 52(4):686-691 disclose immunometric, radioimmunometric, and immunochemiluminometric methods for quantitation of Tg. These methods are all subject to methodological problems such as differences in standardization, variability in interassay sensitivity and precision, hook effects, and interference attributable to Tg antibodies. The problem of interference attributable to Tg antibodies is particularly troubling for clinical application of monitoring Tg levels as a tumor marker because up to 20% of thyroid cancer patients have Tg autoantibodies.

SUMMARY OF THE INVENTION

The present invention provides methods for quantitation of Tg in a sample by mass spectrometry, including tandem mass spectrometry.

In one aspect, methods are provided for determining the amount of Tg in a test sample that include: (a) subjecting a Tg containing test sample to digestion resulting in creation of Tg peptides; (b) purifying one or more Tg peptides; (c) ionizing one or more Tg peptides; (d) detecting the amount of the Tg peptide ion(s) by mass spectrometry; and (e) relating the amount of detected Tg peptide ion(s) to the amount of Tg in the test sample. A preferred enzyme for preparing Tg peptides is trypsin. A suitable Tg peptide for the method is one that can be evaluated by mass spectrometry and can be sufficiently purified from related peptides that may be generated from proteins other than Tg. An example of one such peptide is peptide T129 (sequence VIFDANAPVAVR) (SEQ ID NO: 4) which contains amino acids from positions 1579 to 1590 of Tg, has a molecular weight of about 1,270 Da, and is present in all three isoforms of Tg. See FIG. 4.

Formation of peptide T129 provides a unique trypsin generated peptide for thyroglobulin. Also, creation of peptide T129 from tryptic digestion of Tg should be unaffected by the presence or absence of the Tg antibodies. Thus, measurement of the increase in peptide T129 in a test sample offers a way of quantitating the amount of Tg originally in the test sample free from inference from Tg antibodies.

Any appropriate method may be used to determine the amount of Tg peptide resulting from digestion of Tg in a sample. In the event that a test sample may contain endogenous Tg peptide, steps may be taken to make certain that the endogenous peptide is not confused with peptide generated by digesting Tg in sample. One approach is to remove the endogenous Tg peptide from the sample before digesting Tg. This may done, for example, using a size separation technique. Another approach is to analyze a portion of a test sample according to the claimed methods but excluding the digestion step in order to establish a baseline level for the endogenous peptide in the test sample. In this approach, the once a baseline is determined, it can be subtracted from the post-digestion level of the peptide, the later representing both the endogenous peptide and that generated by digestion.

Because the methods may be applied to complex test samples (particularly body fluids or test samples derived from tissue), steps may be taken to purify Tg in the test sample prior to digestion. This may done, for example, using a size separation technique.

In some embodiments, the methods include generating one or more Tg peptide ions in which at least one of the ions has a mass/charge ratio (m/z) corresponding to that of (singly or multiply charged) peptide T129 ions. In preferred related embodiments, the methods include generating one or more Tg peptide ions in which at least one has m/z of 1272.8±0.5, 636.4±0.5, or 424.3±0.5 (corresponding to singly, doubly, or triply charged peptide T129 ions). In related preferred embodiments, the methods may include generating one or more fragment ions of a Tg peptide ion in which at least one has a m/z of 541.3±0.5, 612.3 35 0.5, 726.4±0.5, 797.4±0.5, 912.4±0.5, or 1059.5±0.5; preferably one or more of the fragment ions are selected from the group consisting of ions with a m/z of 797.4±0.5, 912.4±0.5, and 1059.5±0.5.

In some embodiments, the purification in step (b) is accomplished with at least one size separation technique. Preferably, size separation techniques may be filtration, LC, or any combination thereof. In certain preferred embodiments, the test sample is a body fluid or tissue. In some embodiments, an additional step is included where a second quantity of the test sample is subjected to steps (b) through (e) in order to establish a baseline level of one or more endogenous Tg peptides. In these embodiments, this baseline level can be subtracted from the amount of Tg peptide ion(s) detected in the test sample to determine the amount of Tg peptide ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weigh cut off that allows for retention of Tg above the filter and allows Tg peptides to pass through with the filtrate. In related embodiments, the molecular weigh cut-off is about 2 kD to 300 kD; more preferably about 100 kD to 300 kD. In these embodiments, the two filtrations (pre-digestion and step (b)) may be conducted with the same filter.

In a second aspect, methods are provided for determining the amount of Tg in a test sample that include: (a) subjecting a Tg containing test sample to digestion resulting in creation of peptide T129; (b) purifying peptide T129; (c) ionizing peptide T129 to generate a precursor ion with a m/z of 636.4±0.5; (d) fragmenting the peptide T129 precursor ion to form one or more fragment ions in which at least one has a m/z of about 797.4±0.5, 912.4±0.5, or 1059.5±0.5; detecting the amount of peptide T129 precursor ions, one or more fragment ions, or both, by mass spectrometry; and (e) relating the amount of detected ion(s) to the amount of Tg in the test sample. In certain preferred embodiments, the test sample is a body fluid or tissue or tissue. In some embodiments, an additional step is included where a second quantity of the test sample is subjected to steps (b) through (e) in order to establish a baseline level of one or more endogenous peptide T129. In these embodiments, this baseline level can be subtracted from the amount of peptide T129 ion(s) detected in the test sample to determine the amount of peptide T129 ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weigh cut off that allows for retention of Tg above the filter and allows Tg peptides to pass through with the filtrate. In related embodiments, the molecular weigh cut-off is about 2 kD to 300 kD; more preferably about 100 kD to 300 kD. In these embodiments, the two filtrations (pre-digestion and step (b)) may be conducted with the same filter.

As used herein, the term "purification" or "purifying" does not refer to removing all materials from the sample other than the analyte(s) of interest. Instead, purification refers to a procedure that enriches the amount of one or more analytes of interest relative to one or more other components of the sample. Purification, as used herein, does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

As used herein, the term "about" in reference to quantitative measurements, not including the measurement of mass of an ion, refers to the indicated value plus or minus 10%.

As used herein, the term "substantially all" refers to any proportion greater than 50%, more preferably greater than 60%, more preferably greater than 70%, more preferably greater than 80%, and more preferably greater than 90%.

As used herein, the term "test sample" refers to any sample that may contain Tg. As used herein, the term "body fluid or tissue" means any fluid or tissue that can be isolated from the body of an individual. For example, "body fluid or tissue" may include blood, plasma, serum, bile, saliva, urine, tears, perspiration, and the like. If solid tissue is to be analyzed, it may be processed to release a liquid fraction that could contain any Tg present in the tissue. The liquid fraction can then be subject to the methods described herein.

As used herein, the term "digestion" means proteolytic cleavage of proteins into peptides. Digestion agents may include trypsin, Lyc-C, Arg-R, Asp-N and the like. Digestion is carried out by adding a digestion agent (i.e., an enzyme) to a sample and incubating for some period of time.

As used herein, "Tg" or "Tg molecule" means an intact Tg protein molecule.

As used herein, the term "Tg peptide" means any peptide of 100 amino acids or less that is a fragment of the native Tg. Tg peptides can be endogenous to a test sample or formed as a result of digestion of Tg. Peptide T129 is an example of a Tg peptide formed as a result of trypsin digestion of Tg.

As used herein, the term "size separation technique" means any technique (physical or chemical) that allows for the separation of at least one species from a test sample based on any one or more of molecular weight and shape. Examples of such techniques include, but are not limited to, filtration, chromatography, and certain aspects of mass spectrometry.

As used herein, the term "chromatography" refers to a process in which a chemical mixture carried by a liquid or gas is separated into components as a result of differential distribution of the chemical entities as they flow around, over, and/or through a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "mass spectrometry" or "MS" refers to an analytical technique to identify compounds by their mass. MS refers to methods of filtering, detecting, and measuring ions based on their m/z. MS technology generally includes (1) ionizing the compounds to form charged species (e.g., ions); and (2) detecting the molecular weight of the ions and calculating their m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in positive ion mode" refers to those mass spectrometry methods where positive ions are detected. Similarly, the term "operating in negative ion mode" refers to those mass spectrometry methods where negative ions are detected.

As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e g ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectrometry where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample is interacted with a partially ionized gas at a sufficiently high temperature to atomize and ionize most elements As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification" or "LOQ" refers to the point where measurements become quantitatively meaningful. The analyte response at this LOQ is identifiable, discrete and reproducible with a precision of 20% and an accuracy of 80% to 120%.

In certain preferred embodiments of the methods disclosed herein, mass spectrometry is performed in positive ion mode. In certain particularly preferred embodiments of the methods disclosed herein, mass spectrometry is performed using ESI as the method of creating ions from Tg peptides.

In preferred embodiments, the ions from Tg peptide ionization detectable in a mass spectrometer are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of about 636.4±0.5, and the fragment ions have a m/z of 1059.5±0.5, 921.4±0.5, or 797.4±0.5.

In some preferred embodiments, a separately detectable internal standard peptide (e.g., T129) is introduced in the test sample after trypsin digestion. In these embodiments, all or a portion of the peptide present in the test sample both from digestion of endogenous Tg and the addition of the internal standard are ionized to produce a plurality of ions detectable in a mass spectrometer, and one or more ions produced from the peptide ionization are detected in a mass spectrometer.

In other preferred embodiments, a separately detectable internal Tg standard is provided in the test sample prior to trypsin digestion. In these embodiments, all or a portion of both the endogenous Tg and the internal standard present in the test sample are digested by trypsin resulting in formation of Tg peptides. Tg peptides are ionized to produce a plurality of ions detectable in a mass spectrometer, and one or more ions produced from Tg peptide ionization are detected by mass spectrometry.

In preferred embodiments, the ions detectable in a mass spectrometer produced from the ionization of Tg peptides resulting from Tg digestion are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of 636.4±0.5, and the fragment ions have a m/z of 1059.5±0.5, 921.4±0.5, 797.4±0.5.

In preferred embodiments, the presence or amount of Tg peptide ions is related to the presence or amount of Tg in the original test sample by comparison to a reference Tg sample.

In one embodiment, the methods involve the combination of LC with mass spectrometry. In another preferred embodiment, the mass spectrometry is tandem mass spectrometry (MS/MS).

The summary of the invention described above is non-limiting and other features and advantages of the invention will be apparent from the following detailed description of the invention, and from the claims.

BRIEF DESCRIPTION OF THE DRAWINGS

FIG. 1 shows the amino acid sequence for P01266 (Human Thyroglobulin Precursor) (SEQ ID NO: 1).

FIG. 2 shows the amino acid sequence for P01266-2 (Isoform 2 of P01266) (SEQ ID NO: 2).

FIG. 3 shows the amino acid sequence for Q59GF0 (Thyroglobulin Variant-Fragment) (SEQ ID NO: 3).

FIGS. 4A-4G show a comparison of the three sequences contained in FIGS. 1-3 demonstrating that they all contain amino acids corresponding to positions 1579 to 1590 of Tg. Sequence P01266 is on top (SEQ ID NO: 1); sequence P01266-2 is in the middle (SEQ ID NO: 2); and sequence Q59GF0 is at the bottom (SEQ ID NO: 3). FIG. 4A shows amino acids 1 to 480. FIG. 4B shows amino acids 481 to 960. FIG. 4C shows amino acids 961 to 1380. FIG. 4D shows amino acids 1381 to 1800. FIG. 4E shows amino acids 1801 to 2160. FIG. 4F shows amino acids 2161 to 2520. FIG. 4G shows amino acids 2521 to 2768.

DETAILED DESCRIPTION OF THE INVENTION

Figure 5:
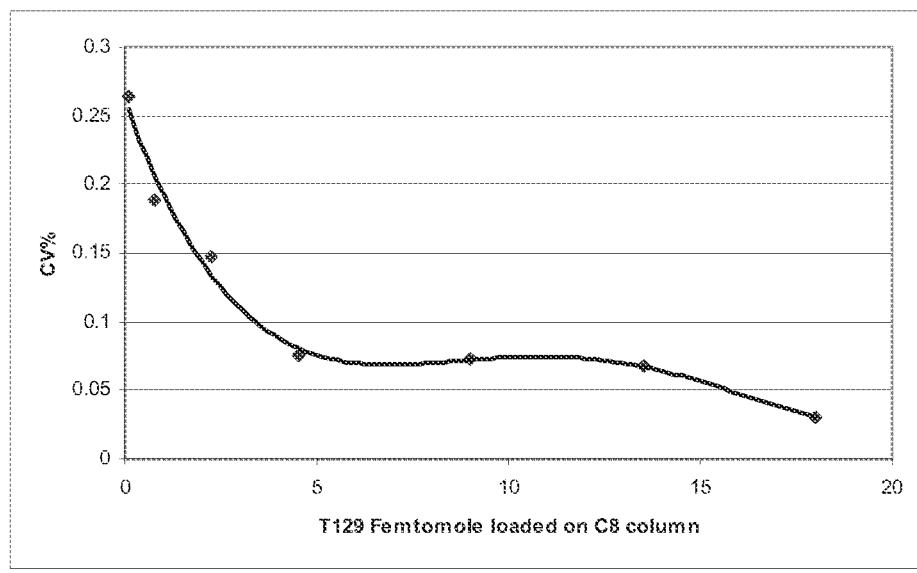
FIG. 5 shows the limit of quantitation verification for Tg peptide ion with m/z corresponding to peptide T129 by MS/MS. The equation describing the trend line for FIG. 5 is as follows: $y = 1E-05x^4 - 0.0007x^3 + 0.0114x^2 - 0.0787x + 0.2606$. $R^2 = 0.9833$ for this fit. Details are described in Example 1.

Methods are described for quantitatively measuring Tg in a test sample. This quantitative measurement is achieved through the use of LC-MS/MS techniques. Prior to the use of LC-MS/MS, samples may be prepared by the following technique, or any portion thereof. A first purification of Tg in a test sample may be conducted through the use of a size separation technique such that substantially all Tg in the test sample is retained. Following the first purification step, enzymatic digestion of Tg may be carried out creating Tg peptides of interest. After digestion, another utilization of a size separation technique may be employed such that a selected Tg peptide generated in the enzymatic digestion of Tg is purified. This second size separation technique can be used to remove substantially all undigested, higher-molecular weight species. Properly executed, the sample preparation techniques ensure that selected Tg peptides quantitated by LC-MS/MS directly result from enzymatic digestion of Tg originally in the test sample; thus, the level of selected Tg peptides in the test sample at the start of LC-MS/MS is directly proportional to the amount of Tg originally present in the test sample.

Any suitable size separation technique may be utilized, but in the examples that follow, both the first and second size separation techniques are filtration through a molecular weight cut-off filter. It is also possible, as discussed in the Examples that follow, to select a molecular weight cut-off filter with an appropriate molecular weight cut-off such that the same filter can be used for both the first size separation and the second size separation.

LC, most preferably HPLC, is utilized, may be utilized either alone or in combination with other purification methods, to purify selected Tg peptides. This purification is combined with MS/MS, thereby providing an assay system for quantifying selected Tg peptides in a test sample. The quantity of the selected Tg peptides in the test sample is then used to determine the quantity of Tg in the original test sample. The Tg quantitation methods provided herein have enhanced specificity and are less subject to methodological problems (such as Tg antibody interference).

Suitable test samples may include any test sample that may contain the analyte of interest. In some preferred embodiments, a sample is a biological sample; that is, a sample obtained from any biological source, such as an animal, a cell culture, an organ culture, and the like. In certain preferred embodiments, samples are obtained from a mammalian animal, such as a dog, cat, horse, etc. Particularly preferred mammalian animals are primates, most preferably humans. Particularly preferred samples include blood, plasma, serum, urine, saliva, tears, cerebrospinal fluid, or other body fluid or tissue samples. Such samples may be obtained, for example, from a patient; that is, a living person presenting oneself in a clinical setting for diagnosis, prognosis, or treatment of a disease or condition. The test sample is preferably obtained from a patient, for example, serum or plasma.

Sample Preparation for Mass Spectrometry

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, centrifugation, combinations thereof and the like. In certain preferred embodiments, Tg present in a test sample prior to enzymatic digestion.

Filtration is one preferred method of preparing a test sample, especially a biological test sample, such as serum or plasma, for chromatography. Such filtration is carried out by filtering a test sample through a molecular weight cut-off filter to separate species with molecular weights higher than the filter's cut-off (including Tg) from those with molecular weights lower than the filter's cut-off. The test sample remaining above the filter following complete (or near complete) filtration is substantially free of potentially interfering species with molecular weights lower than the filter's cut-off.

The pH of the test sample may then be adjusted to any point required by a digestion agent. In certain preferred embodiments, the digestion agent is trypsin and pH can be adjusted with a solution of ammonium acetate to have a pH suitable for this enzyme. In these preferred embodiments, the sample is then digested with trypsin to form Tg peptides (including peptide T129).

After trypsin digestion, the sample may be purified with a second filtration. This post-digestion filtration can be carried out similarly to the pre-digestion filtration described above (with the exception that the filtrate is retained), in order to separate Tg fragments from potentially interfering species with molecular weights higher than the filter's cut-off that may also be present in the sample. The filtrate from this post-digestion filtration can then be purified by liquid chromatography and subsequently subjected to mass spectrometry analysis.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art may select HPLC instruments and columns that are suitable for use in the methods. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-8 bonded groups. The chromatographic column includes an inlet port for receiving a sample and an outlet port for discharging an effluent that includes the fractionated sample.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one embodiment, the sample to be analyzed is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytypic (i.e. mixed) mode. In preferred embodiments, HPLC is performed on an analytical HPLC system with a C8 solid phase using 0.2% formic acid in HPLC Grade Ultra Pure Water and 0.2% formic acid in 100% methanol as the mobile phases.

Numerous column packings are available for chromatographic separation of samples and selection of an appropriate separation protocol is an empirical process that depends on the sample characteristics, analyte of interest, presence of interfering substances and their characteristics, etc. Commercially available HPLC columns include, but are not limited to, polar, ion exchange (both cation and anion), hydrophobic interaction, phenyl, C-2, C-8, C-18, and polar coating on porous polymer columns.

In one embodiment, the HPLC column has a C8 solid phase with a median particle size of 5 µm (nominal) and a median particle pore size of 100 Å. In a preferred embodiment the column dimensions are 1.0 mm ID×50 mm length (Phenomenex Corp. Luna 5µ C8(2) 100 Å New Column 50×1.0 mm, Phenomenex Cat. No. 00B-4249-AO or equivalent).

During chromatography, the separation of materials is effected by variables such as choice of eluent (also known as a "mobile phase"), choice of gradient elution and the gradient conditions, temperature, etc.

Detection and Quantitation by Mass Spectrometry

In various embodiments, Tg peptides may be ionized by any method known to the skilled artisan. Mass spectrometry is performed using a mass spectrometer, which includes an ion source for ionizing the fractionated sample and creating charged molecules for further analysis. Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, Tg peptides are ionized by electrospray ionization (ESI) creating Tg peptide precursor ions. In related preferred embodiments, Tg peptide precursor ions are in a gaseous state and the inert collision gas is argon.

After the sample has been ionized, the positively charged ions thereby created may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). In preferred embodiments, ions are detected using SRM.

Preferably, m/z is determined using a quadrupole instrument. In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps may be combined in methods known as "MS/MS". Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 400 to 1600 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of Tg. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the LC purification and mass spectrometry steps may be performed in an on-line fashion.

In certain embodiments, techniques such as MS/MS are used to isolate precursor ions for further fragmentation. In these embodiments, collision activation dissociation (CAD) may be used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy. In alternative embodiments, electron transfer dissociation (ETD) may be used to generate the fragment ions. In ETD, radical anions are used to transfer electrons to multiply charged peptide or protein cations resulting in random cleavage along the peptide backbone.

In particularly preferred embodiments, Tg is detected and/or quantified using LC-MS/MS as follows. A Tg peptide enriched test sample prepared as described above is subjected to LC. The flow of liquid solvent from the chromatographic column enters the heated nebulizer interface of a LC-MS/MS analyzer and the solvent/analyte mixture is converted to vapor in the heated tubing of the interface. The analyte (e.g., Tg peptides), contained in the nebulized solvent, is ionized by the corona discharge needle of the interface, which applies a large voltage to the nebulized solvent/analyte mixture. The ions (i.e. Tg peptide precursor ions) pass through the orifice of the instrument and enter the first quadrupole. Quadrupoles 1 and 3 (Q1 and Q3) are mass filters, allowing selection of ions (i.e., "precursor" and "fragment" ions) based on their m/z. Quadrupole 2 (Q2) is the collision cell, where ions are fragmented. Q1 selects for ions with m/z of peptide T129 precursor ions (m/z of 636.4±0.5). Selected precursor ions are allowed to pass into the collision chamber (Q2), while ions with any other m/z collide with the sides of Q1 and are eliminated. Precursor ions entering Q2 may be fragmented with collision activated dissociation (CAD) through collisions with neutral argon gas molecules. Alternatively, if the precursor ions entering Q2 are multiply charged cations, they may be fragmented with electron transfer dissociation (ETD). The fragment ions generated are passed into Q3, where selected fragment ions are collected while other ions are eliminated.

Using standard methods well known in the art, one of ordinary skill is capable of identifying one or more fragment ions of a particular Tg peptide precursor ion that may be used for selection in Q3. A specific fragment ion is one that will not be formed in significant amounts by other molecules with similar molecular structures. In contrast, a non-specific fragment ion is one that is formed by molecules other than the desired analyte. Suitable specific fragment ions can be identified by testing various molecular standards to determine whether fragment ions formed by a selected Tg peptide are also formed by other molecules with similar structures or features. Preferably, at least one fragment ion specific for Tg peptide ions with m/z corresponding to that of peptide T129 ions are identified. More preferably, one or more of these fragment ions have m/z of 797.4±0.5, 912.4±0.5 or 1059.5±0.5.

As ions collide with the detector they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of Tg peptides with m/z corresponding to peptide T129. As described above, the relative abundance of a given ion may be converted into an absolute amount of the original analyte using calibration standard curves based on peaks of one or more ions of an internal molecular standard. The absolute amount of an analyte detected by LC-MS/MS can then be converted into an absolute amount of Tg that was present in the original test sample.

The following examples serve to illustrate the invention. These examples are in no way intended to limit the scope of the methods.

EXAMPLES

Example 1: Demonstration of MS Quantitation of Peptide T129

Several samples with various known concentrations of peptide T129 were prepared by series dilution starting with a sample of known peptide T129 concentration. Peptide T129 LOQ and calibration curves were developed from LC-MS/MS analysis of these samples.

LC was performed with a Phenomenex analytical column (Phenomenex Corp. Luna 5μ C8(2) 100 A New Column 50×1.0 mm). A binary HPLC eluent composed of 0.2% formic acid in ultra pure water (HPLC grade) (mobile phase A) and 0.2% formic acid in 100% methanol (mobile phase B) was applied to the analytical column to separate selected Tg peptides from other species contained in the sample. The binary eluent was applied according to the following gradient profile: as a first step, an 80/20 mixture of mobile phase A/mobile phase B was applied for 120 seconds; as a second step, a 30/70 mixture of mobile phase A/mobile phase B was applied for 60 seconds; as a third step, the relative amount of mobile phase B in the mixture was ramped to a 5/95 mixture of mobile phase A/mobile phase B over a period of 120 seconds; as a fourth step, a 5/95 mixture of mobile phase A/mobile phase B was applied for 60 seconds; as a fifth and final step, an 80/20 mixture of mobile phase A/mobile phase B was applied for 240 seconds.

The separated sample was then subjected to MS/MS for quantitation of one or more Tg peptides with m/z corresponding to peptide T129.

MS/MS was performed using a Finnigan TSQ Quantum Ultra MS/MS system (Thermo Electron Corporation). The following software programs all from ThermoElectron were used in the Examples described herein: Tune Master V 1.2 or newer, Xcalibur V 2.0 SR1 or newer, TSQ Quantum 1.4 or newer, LCQuan V 2.0 or newer, and XReport 1.0 or newer. Liquid solvent/analyte exiting the analytical HPLC column flowed to the heated nebulizer interface of a Thermo Finnigan MS/MS analyzer. The solvent/analyte mixture was converted to vapor in the heated tubing of the interface. Analytes in the nebulized solvent were ionized by the corona discharge needle of the interface, which applied voltage to the nebulized solvent/analyte mixture.

Ions passed to the first quadrupole (Q1), which selected ions with a m/z of 636.4±0.5. Ions entering Quadrupole 2 (Q2) collided with argon gas to generate ion fragments, which were passed to quadrupole 3 (Q3) for further selection. Mass transitions used for quantitation of precursor ions with m/z corresponding to peptide T129 during validation on positive polarity are shown in Table 1.

TABLE 1

| Mass transitions for precursor ions with m/z corresponding to peptide T129 (Positive Polarity) | |
|---|---|
| Precursor Ion (m/z) | Fragment Ion (m/z) |
| 636.4 ± 0.5 | 797.4 ± 0.5, 912.4 ± 0.5 & 1059.5 ± 0.5 |

To determine the limit of quantitation (LOQ) with a precision of 20% and an accuracy of 80% to 120%, seven different samples at varying concentrations were assayed and the reproducibility (CV) determined for each. The LOQ for one or more Tg peptides with m/z corresponding to peptide T129 was defined at about 67 amol/μl.

Figure 6:
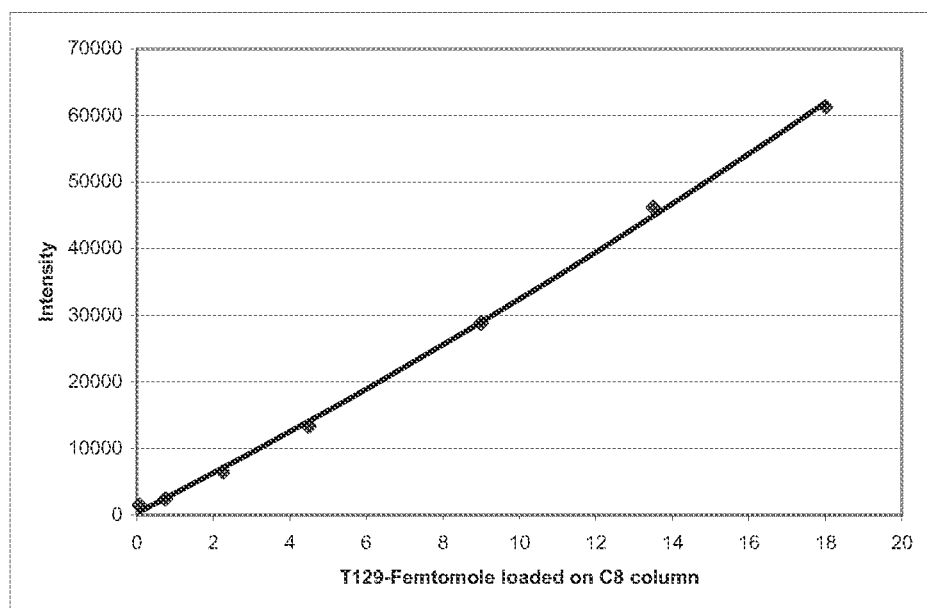
FIG. 6 shows the linearity of the quantitation of peptide T129 in serially diluted stock samples using an LC-MS/MS assay. The equation describing the trend line for FIG. 6 is as follows: $y = 26.919x^2 + 2939.4x + 310.78$. $R^2 = 0.9988$ for this fit. Details are described in Example 1.

Data collected and used to develop the LOQ and Calibration curves in FIGS. 5 and 6 is shown in Table 2.

TABLE 2

Data collected and used to develop LOQ and Calibration curves for peptide T129 in spiked stripped serum samples

| Peptide T129 Concentration (Attomoles/µl) | Femtomoles of peptide T129 in 30 µl sample | Average Ion Counts per Second | CV (%) |
|---|---|---|---|
| 2.5 | 0.075 | 1471.6 | 0.264429 |
| 25 | 0.75 | 2435.6 | 0.188653 |
| 75 | 2.25 | 6455.4 | 0.147946 |
| 150 | 4.5 | 13322.4 | 0.075327 |
| 300 | 9 | 28805 | 0.073374 |
| 450 | 13.5 | 46199.6 | 0.067088 |
| 600 | 18 | 61302.2 | 0.030893 |

Example 2: Demonstration of Quantitation of Peptide T129 in Peptide T129 Spiked Processed, Concentrated and Digested Stripped Serum A 500 µl sample of stripped serum (e.g., the test sample in this Example) was added atop the filter element of a commercially available 300 kDa molecular weight cut-off filter cartridge (Pall Corp. Nanosep 300 kDa, Pall Corp. Cat. No. OD300C33).

The test sample was completely filtered upon centrifugation of the cartridge at 13 kg for 6 minutes. The filtrate was removed and discarded. 500 µl of HPLC grade water was then added to the top of the filter and the cartridge was again centrifuged at 13 kg for 6 minutes. The filtrate was again removed and discarded. Next, 200 µl of 20 mM ammonium acetate was added to the top of the filter. The cartridge was again centrifuged at 13 kg for 3 minutes. The filtrate was again removed and discarded and 100 µl of 20 mM ammonium acetate was added to the top of the filter.

Then, 15 µg of trypsin (Promega Trypsin Gold, Mass Spec Grade, Promega Corp. Cat. No. V5280 or equivalent) was added to the test sample remaining on top of the filter. The resulting mixture was incubated without removal from the filter cartridge at 37 C for up to 17 hours.

After incubation, the filter cartridge was centrifuged at 13 kg for 6 minutes, and the filtrate retained. The filter cartridge was then washed by adding 50 µl of 20 mM ammonium acetate to the top of the filter and centrifuged at 13 kg for 6 minutes. Test samples for analysis by LC-MS/MS were created by pooling the two retained post-digestion filtrates.

The starting volume of stripped serum samples subjected to the above processing and concentration was about 500 µl. The final volume of each pooled post-digestion filtrate was about 130 Thus the above process concentrates samples by a factor of 3.83.

Peptide T129 was then added to the pooled post-digestion filtrates in varying concentrations. 30 µl samples were then analyzed for quantitation of peptide T129 by LC-MS/MS according to the procedure described in Example 1 with the exception that the mass transitions shown in Table 3 were used. The fragment ion with a m/z of 797.4±0.5 was not used due to increased background generated by the processed, concentrated stripped serum.

TABLE 3

Mass transitions for precursor ions with m/z corresponding to peptide T129 from peptide T129 spiked stripped serum samples (Positive Polarity)

| Precursor Ion (m/z) | Fragment Ion (m/z) |
|---|---|
| 636.4 + 0.5 | 912.4 + 0.5 & 1059.5 + 0.5 |

Figure 7:
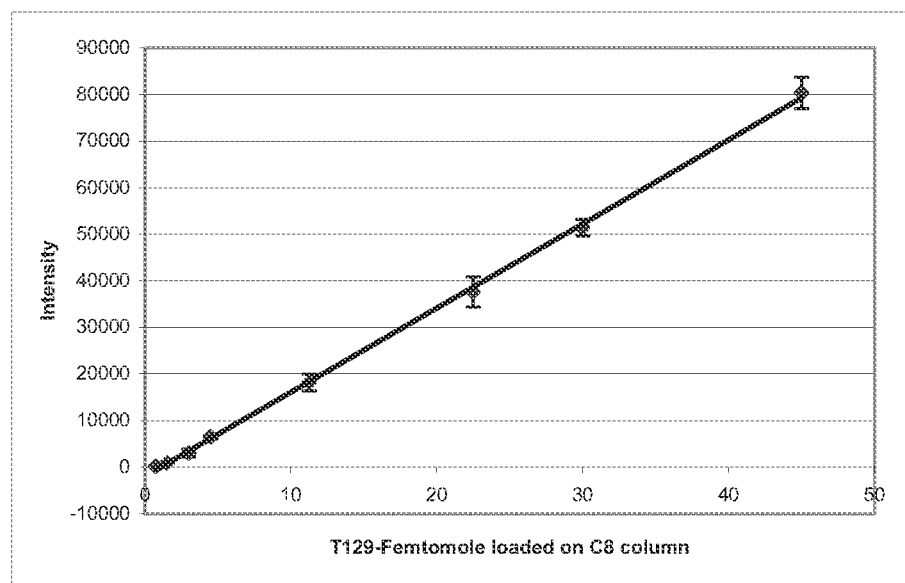
FIG. 7 shows the limit of quantitation verification for peptide T129 in stripped serum by MS/MS. The equation describing the trend line for FIG. 7 is as follows: $y = 1807.2x - 1975$. $R^2 = 0.9993$ for this fit. Details are described in Example 2.
Figure 8:
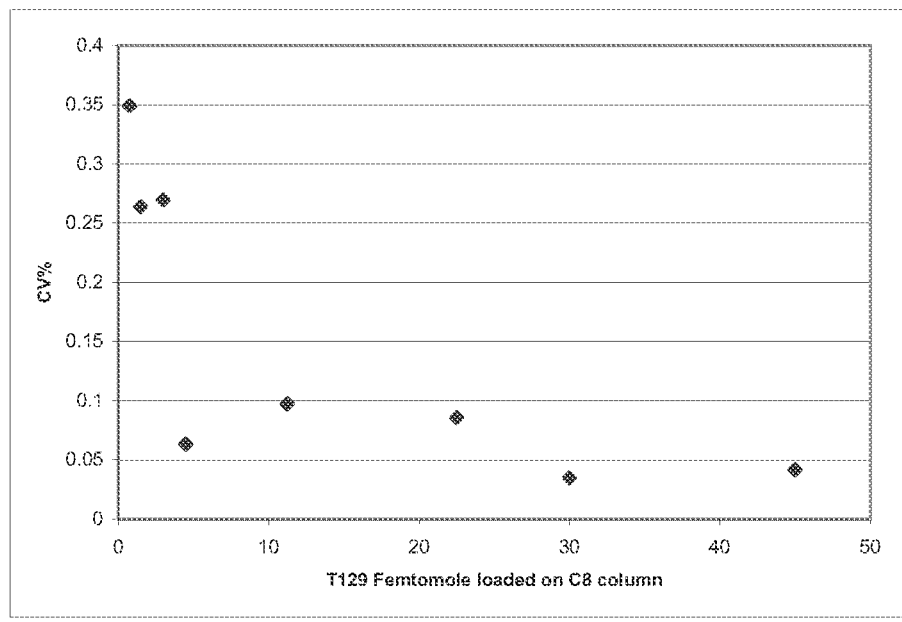
FIG. 8 shows the linearity of the quantitation of peptide T129 in peptide T129 spiked stripped serum using an LC-MS/MS assay. Details are described in Example 2.

Data collected and used to develop the LOQ and Calibration curves found in FIGS. 7 and 8 is shown in Table 4.

TABLE 4

Data collected and used to develop LOQ and Calibration curves for peptide T129

| Femtomoles of Tg in spiked serum sample | Average Ion Counts per Second | CV (%) |
|---|---|---|
| 0.75 | 203 | 0.348839 |
| 1.5 | 957.25 | 0.263782 |
| 3 | 2984.75 | 0.269659 |
| 4.5 | 6504.75 | 0.063318 |
| 11.25 | 18210.5 | 0.097296 |
| 22.5 | 37620 | 0.085823 |
| 30 | 51451 | 0.035083 |

Example 3: Demonstration of Quantitation of Peptide T129 in Stripped Serum Containing Various Concentrations of Added Tg Several 500 µl samples of stripped serum containing various concentrations of added Tg were prepared according to the procedure detailed in Example 2. LC-MS/MS of the resulting test samples was carried out following the steps detailed in Example 1.

Figure 9:
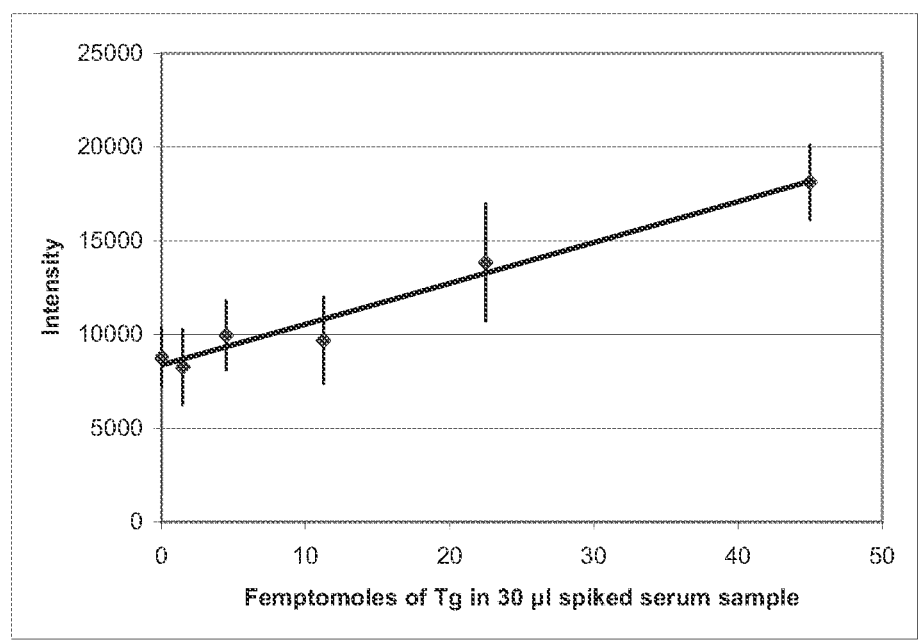
FIG. 9 shows the linearity of the quantitation of Tg peptide ions with m/z corresponding to peptide T129 using an LC-MS/MS assay in stripped serum spiked with Tg prior to processing and concentration according to the methods described herein. The equation describing the trend line for FIG. 9 is as follows: $y = 218.15x + 8363.2$. $R^2 = 0.9681$ for this fit. Details are described in Example 3.

Data collected and used to develop the calibration curve found in FIG. 9 are found in Table 6.

TABLE 6

Data collected and used to develop the calibration curve for peptide T129 MS/MS in Tg spiked stripped serum (processed and condensed as described in Example 3).

| Femtomoles of Tg in spiked serum sample | Average Ion Counts per Second | CV (%) |
|---|---|---|
| 0 | 8784.667 | 0.176987 |
| 1.5 | 8259.5 | 0.246833 |
| 4.5 | 9953.25 | 0.186588 |
| 11.25 | 9696.25 | 0.23816 |
| 22.5 | 13848.25 | 0.225496 |
| 45 | 18125.5 | 0.110826 |

The contents of the articles, patents, patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein.

Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of thyroglobulin in a serum sample, comprising:
   (a) fractionating a serum sample containing thyroglobulin;
   (b) digesting the serum sample containing thyroglobulin with trypsin to generate a thyroglobulin peptide;
   (c) purifying the thyroglobulin peptide;
   (d) ionizing the thyroglobulin peptide to generate one or more ions detectable by mass spectrometry;
   (e) quantifying the amount of the one or more thyroglobulin peptide ions from step (d) by mass spectrometry, wherein the one or more thyroglobulin peptide ions comprise an ion having a mass/charge ratio of 912.4±0.5 and/or an ion having a mass/charge ratio of 1059.5±0.5;
   (f) relating the amount of the one or more thyroglobulin peptide ions to the amount of thyroglobulin in the serum sample.

2. The method of claim 1, wherein the serum sample is taken from a patient suffering from thyroid cancer.

3. The method of claim 1, wherein the mass spectrometry is tandem mass spectrometry.

4. The method of claim 1, wherein the method comprises high performance liquid chromatography (HPLC).

5. The method of claim 1, further comprising using a C18 column.

* * * * *

SEQUENCE LISTING

```
Sequence total quantity: 4
SEQ ID NO: 1            moltype = AA  length = 2768
FEATURE                 Location/Qualifiers
source                  1..2768
                        mol_type = protein
                        organism = Homo sapiens
SEQUENCE: 1
MALVLEIFTL LASICWVSAN IFEYQVDAQP LRPCELQRET AFLKQADYVP QCAEDGSFQT   60
VQCQNDGRSC WCVGANGSEV LGSRQPGRPV ACLSFCQLQK QQILLSGYIN STDTSYLPQC  120
QDSGDYAPVQ CDVQQVQCWC VDAEGMEVYG TRQLGRPKRC PRSCEIRNRR LLHGVGDKSP  180
PQCSAEGEFM PVQCKFVNTT DMMIFDLVHS YNRFPDAFVT FSSFQRRFPE VSGYCHCADS  240
QGRELAETGL ELLLDEIYDT IFAGLDLPST FTETTLYRIL QRRFLAVQSV ISGRFRCPTK  300
CEVERFTATS FGHPYVPSCR RNGDYQAVQC QTEGPCWCVD AQGKEMHGTR QQGEPPSCAE  360
GQSCASERQQ ALSRLYFGTS GYFSQHDLFS SPEKRWASPR VARFATSCPP TIKELFVDSG  420
LLRPMVEGQS QQFSVSENLL KEAIRAIFPS RGLARLALQF TTNPKRLQQN LFGGKFLVNV  480
GQFNLSGALG TRGTFNFSQF FQQLGLASFL NGGRQEDLAK PLSVGLDSNS STGTPEAAKK  540
DGTMNKPTVG SFGFEINLQE NQNALKFLAS LLELPEFLLF LQHAISVPED VARDLGDVME  600
TVLSSQTCEQ TPERLFVPSC TTEGSYEDVQ CFSGECWCVN SWGKELPGSR VRGGQPRCPT  660
DCEKQRARMQ SLMGSQPAGS TLFVPACTSE GHFLPVQCFN SECYCVDAEG QAIPGTRSAI  720
GKPKKCPTPC QLQSEQAFLR TVQALLSNSS MLPTLSDTYI PQCSTDGQWR QVQCNGPPEQ  780
VFELYQRWEA QNKGQDLTPA KLLVKIMSYR EAASGNFSLF IQSLYEAGQQ DVFPVLSQYP  840
SLQDVPLAAL EGKRPQPREN ILLEPYLFWQ ILNGQLSQYP GSYSDFSTPL AHFDLRNCWC  900
VDEAGQELEG MRSEPSKLPT CPGSCEEAKL RVLQFIRETE EIVSASNSSR FPLGESFLVA  960
KGIRLRNEDL GLPPLFPPRE AFAEQFLRGS DYAIRLAAQS TLSFYQRRRF SPDDSAGASA 1020
LLRSGPYMPQ CDAFGSWEPV QCHAGTGHCW CVDEKGGFIP GSLTARSLQI PQCPTTCEKS 1080
RTSGLLSSWK QARSQENPSP KDLFVPACLE TGEYARLQAS GAGTWCVDPA SGEELRPGSS 1140
SSAQCPSLCN VLKSGVLSRR VSPGYVPACR AEDGGFSPVQ CDQAQGSCWC VMDSGEEVPG 1200
TRVTGGQPAC ESPRCPLPFN ASEVVGGTIL CETISGPTGS AMQQCQLLCR QGSWSVFPPG 1260
PLICSLESGR WESQLPQPRA CQRPQLWQTI QTQGHFQLQL PPGKMCSADY ADLLQTFQVF 1320
ILDELTARGF CQIQVKTFGT LVSIPVCNNS SVQVGCLTRE RLGVNVTWKS RLEDIPVASL 1380
PDLHDIERAL VGKDLLGRFT DLIQSGSFQL HLDSKTFPAE TIRFLQGDHF GTSPRTWFGC 1440
SEGFYQVLTS EASQDGLGCV KCPEGSYSQD EECIPCPVGF YQEAGSLAC VPCPVGRTTI 1500
SAGAFSQTHC VTDCQRNEAG LQCDQNGQYR ASQKDRGSGK AFCVDGERR LPWWETEAPL 1560
EDSQCLMMQK FEKVPESKVI FDANAPVAVR SKVPDSEFPV MQCLTDCTED EACSFFTVST 1620
TEPEISCDFY AWTSDNVACM TSDQKRDALG NSKATSFGSL RCQVKVRSHG QDSPAVYLKK 1680
GQGSTTTLQK RFEPTGFQNM LSGLYNPIVF SASGANLTDA HLFCLLACDR DLCCDGFVLT 1740
QVQGGAIICG LLSSPSVLLC NVKDWMDPSE AWANATCPGV TYDQESHQVI LRLGDQEFIK 1800
SLTPLEGTQD TFTNFQQVYL WKDSDMGSRP ESMGCRKDTV PRPASPTEAG LTTELFSPVD 1860
LNQVIVNGNQ SLSSQKHWLF KHLFSAQQAN LWCLSRCVQE HSFCQLAEIT ESASLYFTCT 1920
LYPEAQVCDD IMESNAQGCR LILPQMPKAL FRKKVILEDK VKNFYTRLPF QKLMGISIRN 1980
KVPMSEKSIS NGFFECERRC DADPCCTGFG FLNVSQLKGG EVTCLTLNSL GIQMCSEENG 2040
GAWRILDCGS PDIEVHTYPF GWYQKPIAQN NAPSFCPLVV LPSLTEKVSL DSWQSLALSS 2100
VVVDPSIRHF DVAHVSTAAT SNFSAVRDLC LSECSQHEAC LITTLQTQPG AVRCMFYADT 2160
QSCTHSLQGQ NCRLLLREEA THIYRKPGIS LLSYEASVPS VPISTHGRLL GRSQAIQVGT 2220
SWKQVDQFLG VPYAAPPLAE RRFQAPEPLN WTGSWDASKP RASCWQPGTR TSTSPGVSED 2280
CLYLNVFIPQ NVAPNASVLV FFHNTMDREE SEGWPAIDGS FLAAVGNLIV VTASYRVGVF 2340
GFLSSGSGEV SGNWGLLDQV AALTWVQTHI RGFGGDPRRV SLAADRGGAD VASIHLLTAR 2400
ATNSQLFRRA VLMGGSALSP AAVISHERAQ QQAIALAKEV SCPMSSSQEV VSCLRQKPAN 2460
VLNDAQTKLL AVSGPFHYWG PVIDGHFLRE PPARALKRSL WVEVDLLIGS SQDDGLINRA 2520
KAVKQFEESR GRTSSKTAFY QALQNSLGGE DSDARVEAAA TWYYSLEHST DDYASFSRAL 2580
ENATRDYFII CPIIDMASAW AKRARGNVFM YHAPENYGHG SLELLADVQF ALGLPFYPAY 2640
EGQFSLEEKS LSLKIMQYFS HFIRSGNPNY PYEFSRKVPT FATPWPDFVP RAGGENYKEF 2700
SELLPNRQGL KKADCSFWSK YISSLKTSAD GAKGGQSAES EEEELTAGSG LREDLLSLQE 2760
PGSKTYSK                                                         2768

SEQ ID NO: 2            moltype = AA  length = 2711
FEATURE                 Location/Qualifiers
source                  1..2711
                        mol_type = protein
```

```
                    organism = Homo sapiens
SEQUENCE: 2
MALVLEIFTL LASICWVSAN IFEYQVDAQP LRPCELQRET AFLKQADYVP QCAEDGSFQT    60
VQCQNDGRSC WCVGANGSEV LGSRQPGRPV ACLSFCQLQK QQILLSGYIN STDTSYLPQC   120
QDSGDYAPVQ CDVQQVQCWC VDAEGMEVYG TRQLGRPKRC PRSCEIRNRR LLHGVGDKSP   180
PQCSAEGEFM PVQCKFVNTT DMMIFDLVHS YNRFPDAFVT FSSFQRRFPE VSGYCHCADS   240
QGRELAETGL ELLLDEIYDT IFAGLDLPST FTETTLYRIL QRRFLAVQSV ISGRFRCPTK   300
CEVERFTATS FGHPYVPSCR RNGDYQAVQC QTEGPCWCVD AQGKEMHGTR QQGEPPSCAE   360
GQSCASERQQ ALSRLYFGTS GYFSQHDLFS SPEKRWASPR VARFATSCPP TIKELFVDSG   420
LLRPMVEGQS QQFSVSENLL KEAIRAIFPS RGLARLALQF TTNPKRLQQN LFGGKFLVNV   480
GQFNLSGALG TRGTFNFSQF FQQLGLASFL NGGRQEDLAK PLSVGLDSNS STGTPEAAKK   540
DGTMNKPTVG SFGFEINLQE NQNALKFLAS LLELPEFLLF LQHAISVPED VARDLGDVME   600
TVLSSQTCEQ TPERLFVPSC TTEGSYEDVQ CFSGECWCVN SWGKELPGSR VRGGQPRCPT   660
DCEKQRARMQ SLMGSQPAGS TLFVPACTSE GHFLPVQCFN SECYCVDAEG QAIPGTRSAI   720
GKPKKCPTPC QLQSEQAFLR TVQALLSNSS MLPTLSDTYI PQCSTDGQWR QVQCNGPPEQ   780
VFELYQRWEA QNKGQDLTPA KLLVKIMSYR EAASGNFSLF IQSLYEAGQQ DVFPVLSQYP   840
SLQDVPLAAL EGKRPQPREN ILLEPYLFWQ ILNGQLSQYP GSYSDFSTPL AHFDLRNCWC   900
VDEAGQELEG MRSEPSKLPT CPGSCEEAKL RVLQFIRETE EIVSASNSSR FPLGESFLVA   960
KGIRLRNEDL GLPPLFPPRE AFAEQFLRGS DYAIRLAAQS TLSFYQRRRF SPDDSAGASA  1020
LLRSGPYMPQ CDAFGSWEPV QCHAGTGHCW CVDEKGGFIP GSLTARSLQI PQCPTTCEKS  1080
RTSGLLSSWK QARSQENPSP KDLFVPACLE TGEYARLQAS GAGTWCVDPA SGEELRPGSS  1140
SSAQCPSLCN VLKSGVLSRR VSPGYVPACR AEDGGFSPVQ CDQAQGSCWC VMDSGEEVPG  1200
TRVTGGQPAC ESPRCPLPFN ASEVVGGTIL CETISGPTGS AMQQCQLLCR QGSWSVFPPG  1260
PLICSLESGR WESQLPQPRA CQRPQLWQTI QTQGHFQLQL PPGKMCSADY ADLLQTFQVF  1320
ILDELTARGF CQIQVKTFGT LVSIPVCNNS SVQVGCLTRE RLGVNVTWKS RLEDIPVASL  1380
PDLHDIERAL VGKDLLGRFT DLIQGSFQL HLDSKTFPAE TIRFLQGDHF GTSPRTWFGC  1440
SEGFYQVLTS EASQDGLGCV KCPEGSYSQD EECIPCPVGF YQEQAGSLAC VPCPVGRTTI  1500
SAGAFSQTHL MQKFEKVPES KVIFDANAPV AVRSKVPDSE FPVMQCLTDC TEDEACSFFT  1560
VSTTEPEISC DFYAWTSDNV ACMTSDQKRD ALGNSKATSF GSLRCQVKVR SHGQDSPAVY  1620
LKKGQGSTTT LQKRFEPTGF QNMLSGLYNP IVFSASGANL TDAHLFCLLA CDRDLCCDGF  1680
VLTQVQGGAI ICGLLSSPSV LLCNVKDWMD PSEAWANATC PGVTYDQESH QVILRLGDQE  1740
FIKSLTPLEG TQDTFTNFQQ VYLWKDSDMG SRPESMGCRK DTVPRPASPT EAGLTTELFS  1800
PVDLNQVIVN GNQSLSSQKH WLFKHLFSAQ QANLWCLSRC VQEHSFCQLA EITESASLYF  1860
TCTLYPEAQV CDDIMESNAQ GCRLILPQMP KALFRKKVIL EDKVKNFYTR LPFQKLMGIS  1920
IRNKVPMSEK SISNGFFECE RRCDADPCCT GFGFLNVSQL KGGEVTCLTL NSLGIQMCSE  1980
ENGGAWRILD CGSPDIEVHT YPFGWYQKPI AQNNAPSFCP LVVLPSLTEK VSLDSWQSLA  2040
LSSVVVDPSI RHFDVAHVST AATSNFSAVR DCLSECSQH EACLITTQT QPGAVRCMFY  2100
ADTQSCTHSL QGQNCRLLLR EEATHIYRKP GISLLSYEAS VPSVPISTHG RLLGRSQAIQ  2160
VGTSWKQVDQ FLGVPYAAPP LAERRFQAPE PLNWTGSWDA SKPRASCWQP GTRTSTSPGV  2220
SEDCLYLNVF IPQNVAPNAS VLVFFHNTMD REESEGWPAI DGSFLAAVGN LIVVTASYRV  2280
GVFGFLSSGS GEVSGNWGLL DQVAALTWVQ THIRGFGGDP RRVSLAADRG GADVASIHLL  2340
TARATNSQLF RRAVLMGGSA LSPAAVISHE RAQQQAIALA KEVSCPMSSS QEVVSCLRQK  2400
PANVLNDAQT KLLAVSGPFH YWGPVIDGHF LREPPARALK RSLWVEVDLL IGSSQDDGLI  2460
NRAKAVKQFE ESRGRTSSKT AFYQALQNSL GGEDSDARVE AAATWYYSLE HSTDDYASFS  2520
RALENATRDY FIICPIIDMA SAWAKRARGN VFMYHAPENY GHGSLELLAD VQFALGLPFY  2580
PAYEGQFSLE EKSLSLKIMQ YFSHFIRSGN PNYPYEFSRK VPTFATPWPD FVPRAGGENY  2640
KEFSELLPNR QGLKKADCSF WSKYISSLKT SADGAKGGQS AESEEEELTA GSGLREDLLS  2700
LQEPGSKTYS K                                                       2711

SEQ ID NO: 3          moltype = AA  length = 1574
FEATURE               Location/Qualifiers
source                1..1574
                      mol_type = protein
                      organism = Homo sapiens
SEQUENCE: 3
IPRKPISKRP VRPSLPRSPR CPLPFNASEV VGGTILCETI SGPTGSAMQQ CQLLCRQGSW    60
SVFPPGPLIC SLESGRWESQ LPQPRACQRP QLWQTIQTQG HFQLQLPPGK MCSADYAGLL   120
QTFQVFILDE LTARGFCQIQ VKTFGTLVSI PVCNNSSVQV GCLTRERLGV NVTWKSRLED   180
IPVASLPDLH DIERALVGKD LLGRFTDLIQ SGSFQLHLDS KTFPAETIRF LQGDHFGTSP   240
RTWFGCSEGF YQVLTSEASQ DGLGCVKCPE GSYSQDEECI PCPVGFYQEQ AGSLACVPCP   300
VGRTTISAGA FSQTHCVTDC QRNEAGLQCD QNGQYRASQK DRGSGKAFCV DGEGRRLPWW   360
ETEAPLEDSQ CLMMQKFEKV PESKVIFDAN APVAVRSKVP DSEFPVMQCL TDCTEDEACS   420
FFTVSTTEPE ISCDFYAWTS DNVACMTSDQ KRDALGNSKA TSFGSLRCQV KVRSHGQDSP   480
AVYLKKGQGS TTTLQKRFEP TGFQNMLSGL YNPIVFSASG ANLTDAHLFC LLACDRDLCC   540
DGFVLTQVQG GAIICGLLSS PSVLLCNVKD WMDPSEAWAN ATCPGVTYDQ ESHQVILRLG   600
DQEFIKSLTP LEGTQDTFTN FQQVYLWKDS DMGSRPESMG CRKNTVPRPA SPTEAGLTTE   660
LFSPVDLNQV IVNGNQSLSS QKHWLFKHLF SAQQANLWCL SRCVQEHSFC QLAEITESAS   720
LYFTCTLYPE AQVCDDIMES NAQGCRLLIP QMPKALFRKK VILEDKVKNF YTRLPFQKLT   780
GISIRNKVPM SEKSISNGFF ECERRCDADP CCTGFGFLNV SQLKGGEVTC LTLNSLGIQM   840
CSEENGGAWR ILDCGSPDIE VHTYPFGWYQ KPIAQNNAPS FCPLVVLPSL TEKVSLDSWQ   900
SLALSSVVVD PSIRHFDVAH VSTAATSNFS AVRDCLSEC SQHEACLITT LQTPGAVRC   960
MFYADTQSCT HSLQGQNCRL LLREEATHIY RKPGISLLSY EASVPSVPIS THGRLLGRSQ  1020
AIQVGTSWKQ VDQFLGVPYA APPLAERRFQ APEPLNWTGS WDASKPRASC WQPGTRTSTS  1080
PGVSEDCLYL NVFIPQNVAP NASVLVFFHN TMDREESEGW PAIDGSFLAA VGNLIVVTAS  1140
YRVGVFGFLS SGSGEVSGNW GLLDQVAALT WVQTHIRGFG GDPRRVSLAA DRGGADVASI  1200
HLLTARATNS QLFRRAVLMG GSALSPAAVI SHERAQQQAI ALAKEVSCPM SSSQEVVSCL  1260
RQKPANVLND AQTKLLAVSG PFHYWGPVID GHFLREPPAR ALKRSLWVEV DLLIGSSQDD  1320
GLINRAKAVK QFEESQGRTS SKTAFYQALQ NSLGGEDSDA RVEAAATWYY SLEHSTDDYA  1380
SFSRALENAT RDYFIICPII DMASAWAKRA RGNVFMYHAP ENYGHGSLEL LADVQFALGL  1440
```

```
PFYPAYEGQF SLEEKSLSLK IMQYFSHFIR SGNPNYPYEF SRKVPTFATP WPDFVPRAGG   1500
ENYKEFSELL PNRQGLKKAD CSFWSKYISS LKTSADGAKG GQSAESEEEE LTAGSGLRED   1560
LLSLQEPGSK TYSK                                                    1574

SEQ ID NO: 4            moltype = AA  length = 12
FEATURE                 Location/Qualifiers
source                  1..12
                        mol_type = protein
                        organism = Homo sapiens
SEQUENCE: 4
VIFDANAPVA VR                                                      12
```